United States Patent
Nakatani et al.

(10) Patent No.: US 8,257,962 B2
(45) Date of Patent: Sep. 4, 2012

(54) EXTRACELLULAR POTENTIAL MEASURING DEVICE AND ITS MANUFACTURING METHOD

(75) Inventors: Masaya Nakatani, Hyogo (JP); Hiroaki Oka, Osaka (JP); Fumiaki Emoto, Osaka (JP)

(73) Assignee: Panasonic Corporation, Osaka (JP)

( * ) Notice: Subject to any disclaimer, the term of this patent is extended or adjusted under 35 U.S.C. 154(b) by 2144 days.

(21) Appl. No.: 10/513,392

(22) PCT Filed: Mar. 8, 2004

(86) PCT No.: PCT/JP2004/002951
§ 371 (c)(1),
(2), (4) Date: Nov. 4, 2004

(87) PCT Pub. No.: WO2004/079354
PCT Pub. Date: Sep. 16, 2004

(65) Prior Publication Data
US 2005/0221469 A1    Oct. 6, 2005

(30) Foreign Application Priority Data

Mar. 7, 2003 (JP) .................................. 2003-062228
Mar. 7, 2003 (JP) .................................. 2003-062229

(51) Int. Cl.
*C12M 1/42*  (2006.01)
*C12M 3/00*  (2006.01)
*C12N 13/00* (2006.01)

(52) U.S. Cl. ............... 435/285.2; 435/173.1; 435/173.4; 435/173.5; 435/173.6; 435/288.3; 435/288.4

(58) Field of Classification Search .............. 435/285.2, 435/173.1, 173.4, 173.5, 173.6, 288.3, 288.4
See application file for complete search history.

(56) References Cited

U.S. PATENT DOCUMENTS

| | | | |
|---|---|---|---|
| 6,413,792 B1 * | 7/2002 | Sauer et al. | 438/49 |
| 6,627,067 B1 * | 9/2003 | Branton et al. | 205/778 |
| 6,682,649 B1 * | 1/2004 | Petersen et al. | 205/777.5 |
| 6,984,297 B2 * | 1/2006 | Nisch et al. | 204/403.01 |
| 2002/0063067 A1 | 5/2002 | Bech et al. | |
| 2002/0182627 A1 * | 12/2002 | Wang et al. | 435/6 |
| 2003/0080314 A1 * | 5/2003 | Nisch et al. | 252/62.2 |

(Continued)

FOREIGN PATENT DOCUMENTS

DE    197 12 309    5/1998

(Continued)

*Primary Examiner* — Nathan Bowers
(74) *Attorney, Agent, or Firm* — Wenderoth, Lind & Ponack, L.L.P.

(57) ABSTRACT

An extracellular potential measuring device includes a plate portion having a first surface and a second surface opposite to the first surface, and an electrode provided on the second surface of the plate portion. In the plate portion, a pocket having an opening which opens to the first surface is formed, and a through-hole communicating to the second surface from the pocket. The through-hole communicates from a position which is closer to the opening than a deepest point of the first pocket. The electrode is provided around of the opening of the through-hole. In this device, even if a cell to be examined does not reach the deepest point of the pocket, a cell membrane of the cell can tightly attaches onto the through-hole securely without a clearance. Hence, culture solution inside the through-hole is isolated from culture solution over an upper surface of the plate portion, thereby allowing electrochemical changes caused by activities of the cell to be detected efficiently with a detector electrode.

61 Claims, 28 Drawing Sheets

U.S. PATENT DOCUMENTS

2003/0153067 A1 * 8/2003 Stett et al. .................. 435/285.2

FOREIGN PATENT DOCUMENTS

| | | |
|---|---|---|
| DE | 199 48 473 | 4/2001 |
| EP | 0 652 308 B1 | 5/1995 |
| EP | 1 352 952 | 10/2003 |
| JP | 6-244257 | 9/1994 |
| JP | 2004-012215 | 1/2004 |
| JP | 2004-069309 | 3/2004 |
| WO | 01/25769 | 4/2001 |
| WO | 01/48474 | 7/2001 |
| WO | 02/03058 | 1/2002 |
| WO | 02/055653 | 7/2002 |

* cited by examiner

EXTRACELLULAR POTENTIAL MEASURING DEVICE AND ITS MANUFACTURING METHOD

TECHNICAL FIELD

The present invention relates to an extracellular potential measuring device for measuring extracellular potentials or physicochemical changes caused by activities of cells, and a method for manufacturing the device. The device is used, e.g. in drug screening to detect cell reactions in response to chemical substances.

BACKGROUND ART

Conventionally, in developing new drugs, candidate drugs are screened by patch clamping or a method using a fluorescent pigment or a light emitting indicator, while using cell electrical activities as indexes.

In the patch clamping, ion transport via a single channel protein molecule in a small portion, a patch, of a cell membrane attached to a tip of a micropipette is electrically recorded with a microelectrode probe. This is one of a few methods that can be used to examine functions of a single protein molecule in real time (See, e.g. Molecular Biology of the Cell, Third Edition, Garland Publishing Inc., New York, 1994, Bruce Alberts et al., Japanese Version, Saibou no Bunshi Seibutugaku Dai San Pan pp. 181-182, 1995, Kyoikusha).

Alternatively, it is possible to employ the aforementioned method using a fluorescent pigment or a light emitting indicator which emits light in response to concentration changes in a specific ion so as to measure cell electrical activities while monitoring intracellular ion transport.

However, the patch clamping requires special techniques for preparation and manipulation of a micropipette and also much time for measuring one sample. Hence, the patch clamping is not suitable for screening many drug candidate compounds at high speed. On the other hand, the method using a fluorescent pigment or the like can screen many drug candidate compounds at high speed; however, it requires a process of staining cells, and pigments not only discolor the background, but also are decolorized with time during measurement, thus resulting in a inferior S/N ratio.

WO02/055653 discloses a conventional device for measuring extracellular potentials, including a substrate having a unit for holding cells, and electrodes on the unit. This device can provide the same high quality of data as those obtained by the patch clamping, and also can measure many samples at high speed and as easily as the method using a fluorescent pigment.

An operation of the conventional extracellular potential measuring device will be described in detail as follows with reference to accompanying drawings.

FIG. 45 shows a cross sectional view of conventional extracellular potential measuring device 49. Well 40 contains culture solution 48A, and examined cell 47 is captured and held in a cell holder provided on substrate 42. The cell holder consists of pocket 41 provided in substrate 42, and through-hole 44 linked with pocket 41 via opening 44A. Through-hole 44 contains measuring electrode 45 as a sensor for outputting a potential of culture solution 48B inside through-hole 44 via wiring.

During measurement, cell 47 to be examined is tightly held in opening 41A of pocket 41 by a suction pump from a side towards through-hole 44. Then, electric signal 49A generated by activities of cell 47 is detected by measuring electrode 45 provided inside through-hole 44 without leaking into culture solution 48A inside well 40.

In this conventional extracellular potential measuring device 49, through-hole 44 is formed at the deepest point of pocket 41. For this structure, even when cell 47 is held inside pocket 41, if a cell membrane adheres onto a portion pocket 41 other than opening 41A, culture solution 48B inside through-hole 44 is electrically conducted with culture solution 48A inside well 40, hence preventing high precision measurement.

It is also impossible to examine whether or not cell 47 is held in pocket 41 and whether or not the cell membrane adheres as to cover through-hole 44.

Substrate 42 has two openings 41A and 41B having different diameters in both sides thereof. Opening 41A of pocket 41 for holding cell 47 has a diameter ranging about from 10 to 30 μm, and opening 44B of through-hole 44 opening on substrate 42 has a diameter ranging from 1 to 5 μm. Accurate formation of this structure requires two masks. The first mask is used to form pocket 41 by dry etching by photolithography, and then the second mask is used to form through-hole 44 by dry etching by photolithography.

However, conventional device 49 requires time to manufacture inexpensively since the masks may be misaligned during the dry etching after the dry etching, and since the masks require separate dry etchings.

Conventional device 49 also requires at least one of a pressurizing of culture solution 48A from well 40 and a depressurizing of culture solution 48B inside through-hole 44 in order to keep cell 47 inside pocket 41. At this moment, culture solution 48B needs to be introduced by a pressure difference into pocket 41 so as to contact measuring electrode 45. The pressure difference may be determined to be an appropriate value, hence allowing culture solution 48B to form a meniscus shape at opening 44B of through-hole 44 stably.

At opening 44B having a straight line shape shown in FIG. 45, the appropriate pressure difference capable of forming a meniscus shape of culture solution 48B ranges in a narrow range. In other words, a slight deviation of the pressure difference from the optimum values breaks the meniscus shape, thereby failing to keep culture solution 48B in a constant quantity.

SUMMARY OF THE INVENTION

An extracellular potential measuring device includes a plate portion having a first surface and a second surface opposite to the first surface, and an electrode provided on the second surface of the plate portion. In the plate portion, a pocket having an opening which opens to the first surface is formed, and a through-hole communicating to the second surface from the pocket. The through-hole communicates from a position which is closer to the opening than a deepest point of the first pocket. The electrode is provided around of the opening of the through-hole.

In this device, even if a cell to be examined does not reach the deepest point of the pocket, a cell membrane of the cell can tightly attaches onto the through-hole securely without a clearance. Hence, culture solution inside the through-hole is isolated from culture solution over a upper surface of the plate portion, thereby allowing electrochemical changes caused by activities of the cell to be detected efficiently with a detector electrode.

DETAILED DESCRIPTION OF PREFERRED EMBODIMENTS

Exemplary Embodiment 1

Figure 1:
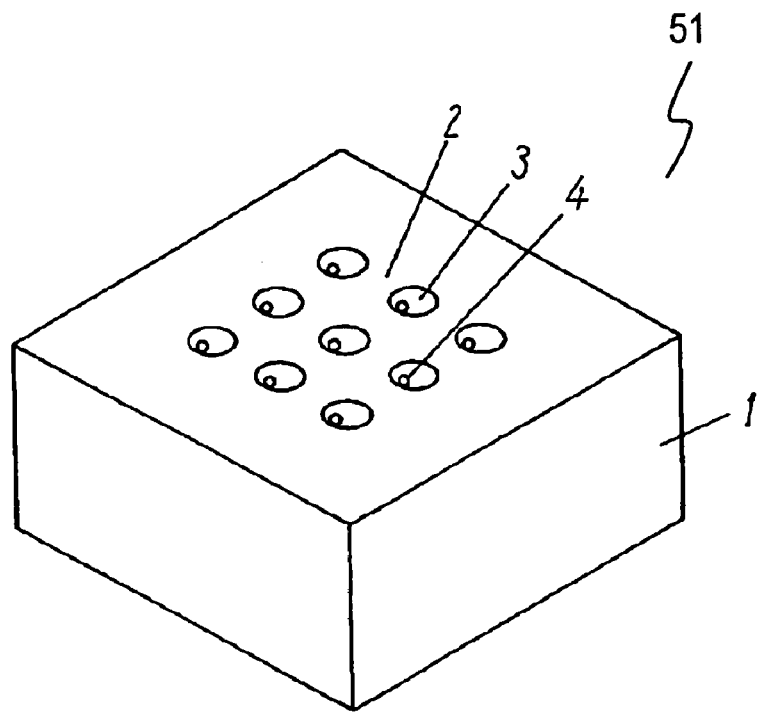
FIG. 1 is a perspective view of an extracellular potential measuring device according to Exemplary Embodiment 1 of the present invention.
Figure 2:
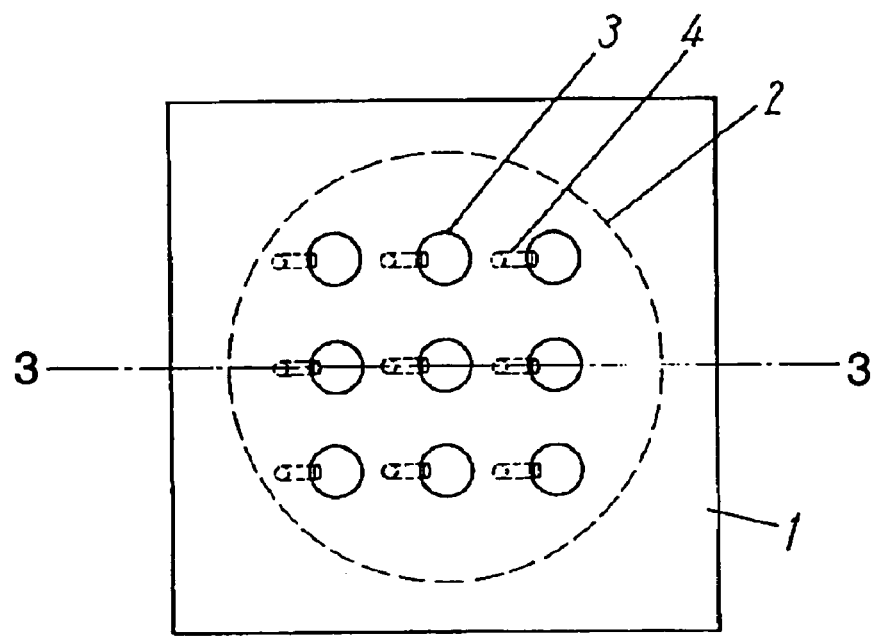
FIG. 2 is a plan view of the extracellular potential measuring device according to Embodiment 1.
Figure 3:
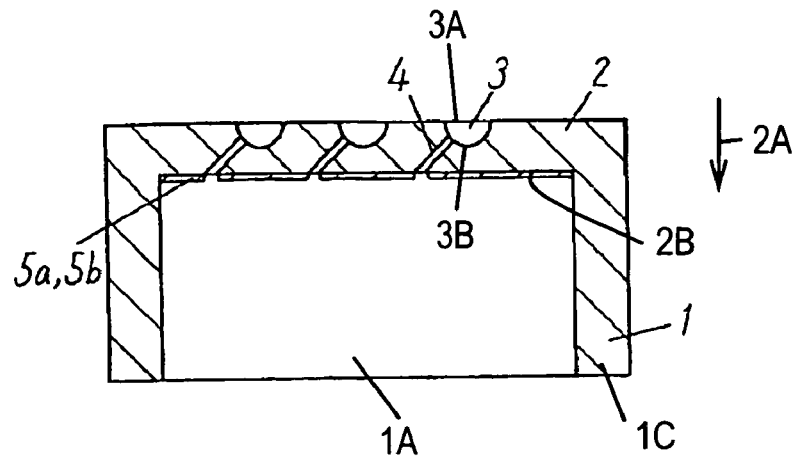
FIG. 3 is a cross sectional view of the extracellular potential measuring device according to Embodiment 1.
Figure 5:
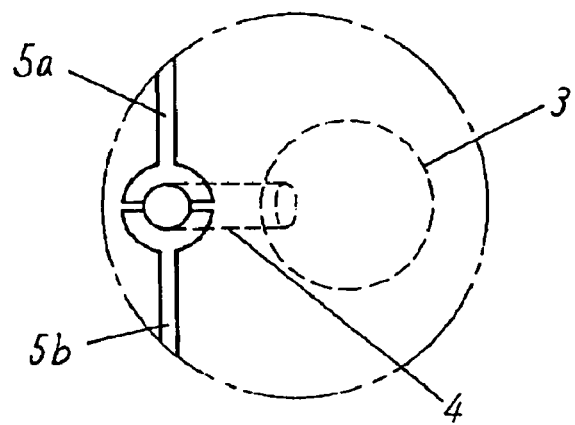
FIG. 5 is an enlarged view of an essential part of the extracellular potential measuring device according to Embodiment 1.
Figure 20:
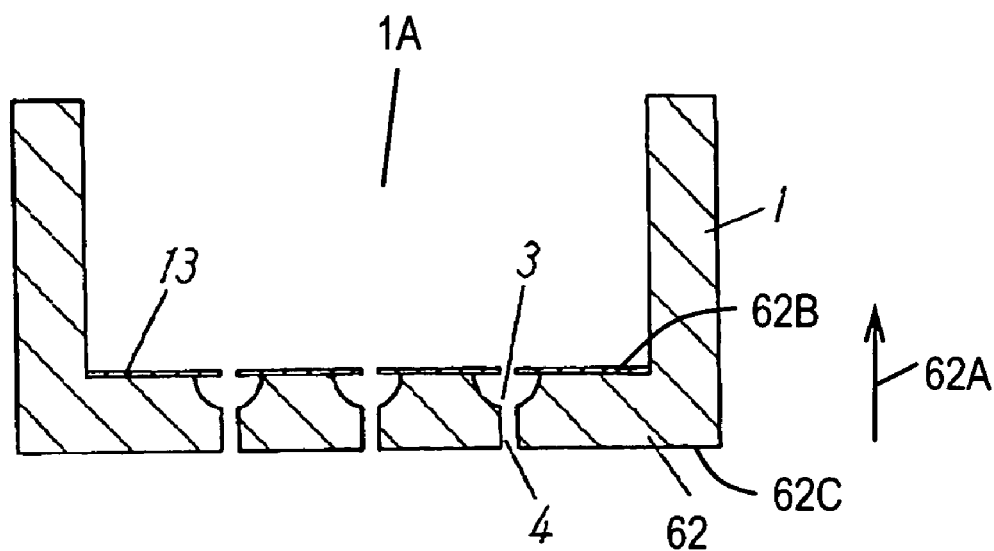
FIG. 20 is a cross sectional view of another extracellular potential measuring device according to Embodiment 1.
Figure 21:
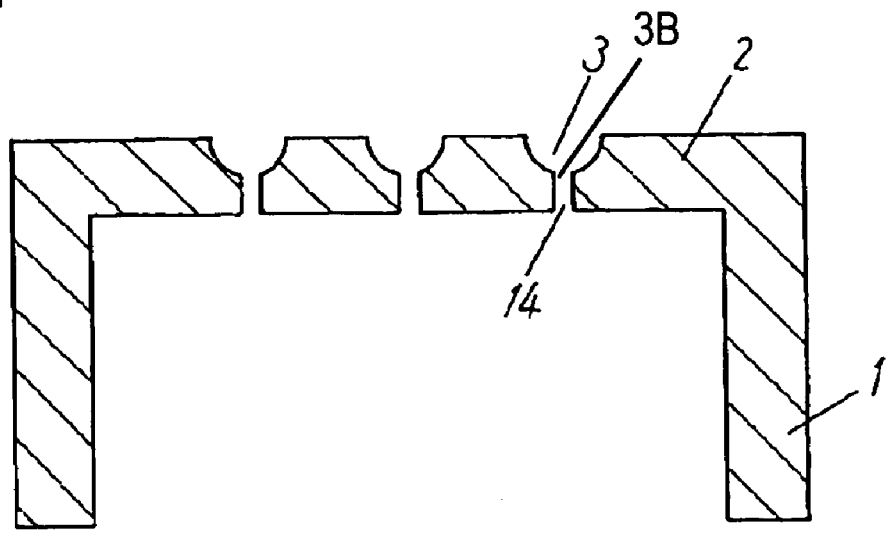
FIG. 21 is a cross sectional view of a further extracellular potential measuring device according to Embodiment 1.
Figure 22:
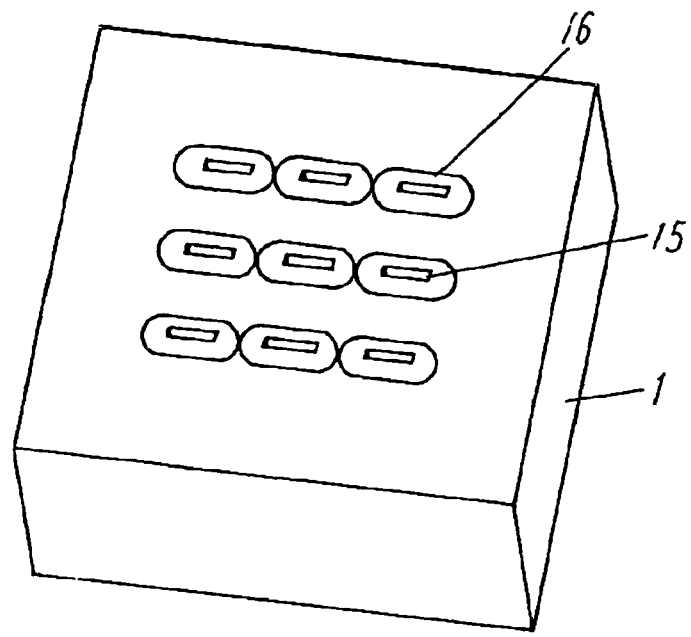
FIG. 22 is a perspective view of the extracellular potential measuring device shown in FIG. 21.
Figure 23:
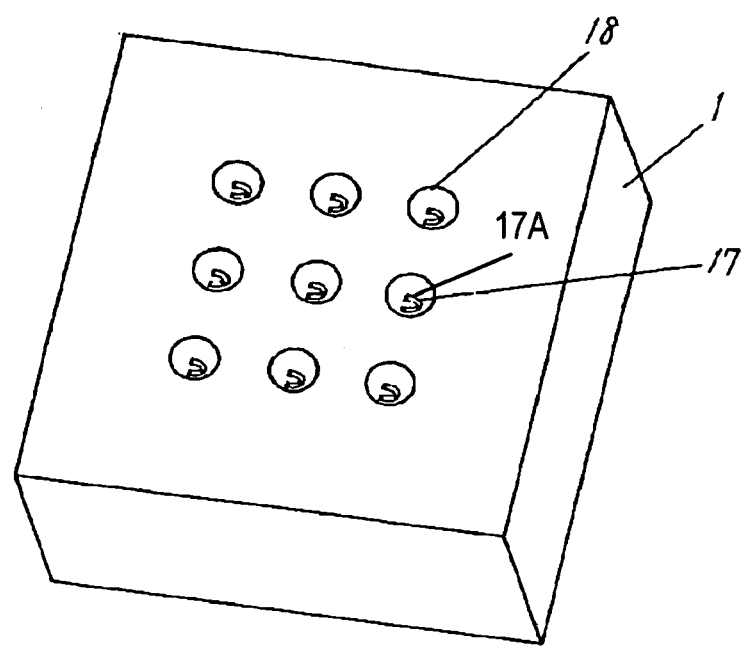
FIG. 23 is a perspective view of the extracellular potential measuring device shown in FIG. 21.

FIG. 1 is a perspective view of extracellular potential measuring device 51 according to Exemplary Embodiment 1 of the present invention. FIG. 2 is a plan view of device 51, and FIG. 3 is a cross sectional view of device 51 taken along line 3-3 shown in FIG. 2. FIG. 5 is an enlarged view of device 51. FIGS. 12 to 21 are cross sectional views of device 51 for illustrating a method for manufacturing the device. FIGS. 22 and 23 are perspective views of another extracellular potential measuring device according to Embodiment 1.

As shown in FIG. 1 to FIG. 3, substrate 1 made of silicon has recess 1A and ridge 1C. Plate portion 2 is formed as a part of substrate 1 and supported by ridge 1C. Plate portion 2 is made of material identical to that of substrate 1, silicon, and has a thickness of about 25 μm. Pocket 3 has a semispherical surface and has opening 3A having a diameter of about 20 μm and opening from the surface of substrate 1. Pocket 3 is linked with through-hole 4 having a uniform cross section along its whole length in the longitudinal direction to pass through plate portion 2. As shown in FIG. 3, through-hole 4 is formed at a position closer to opening 3A than deepest point 3B of pocket 3 and inclines at about 45° with respect to thickness direction 2A of plate portion 2. The cross section of through-holes 4 has either a circle shape having a diameter of about 5 μm or an oval shape having a long diameter of about 5 μm.

As shown in FIG. 5, detector electrodes 5a and 5b are formed at in a circumference of the opening of through-hole 4.

An operation of extracellular potential measuring device 51 will be described. FIG. 6 to FIG. 9A are enlarged cross sectional views of an essential part of device 51 for illustrating the operation.

Figure 6:
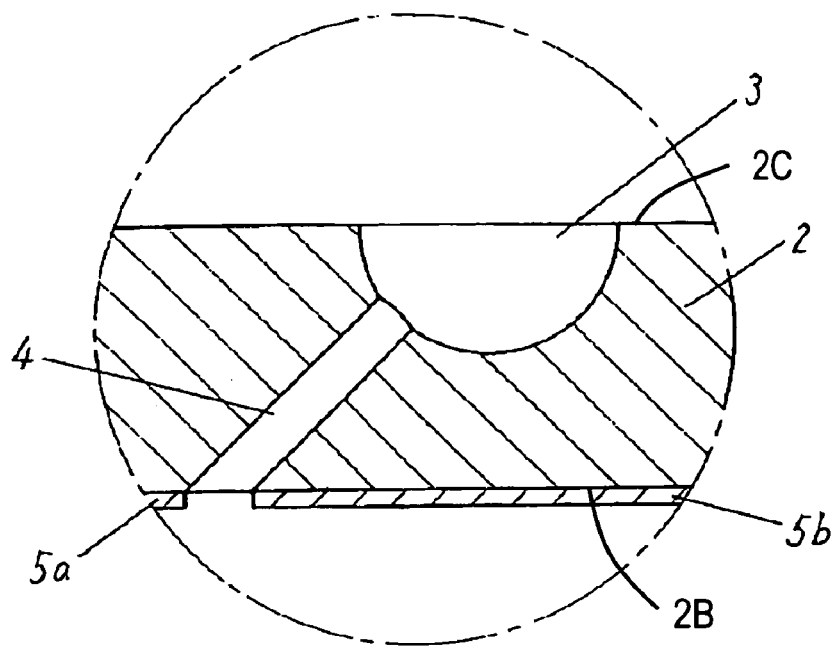
FIG. 6 is an enlarged cross sectional view of an essential part of the extracellular potential measuring device for illustrating an operation of the device according to Embodiment 1.
Figure 7:
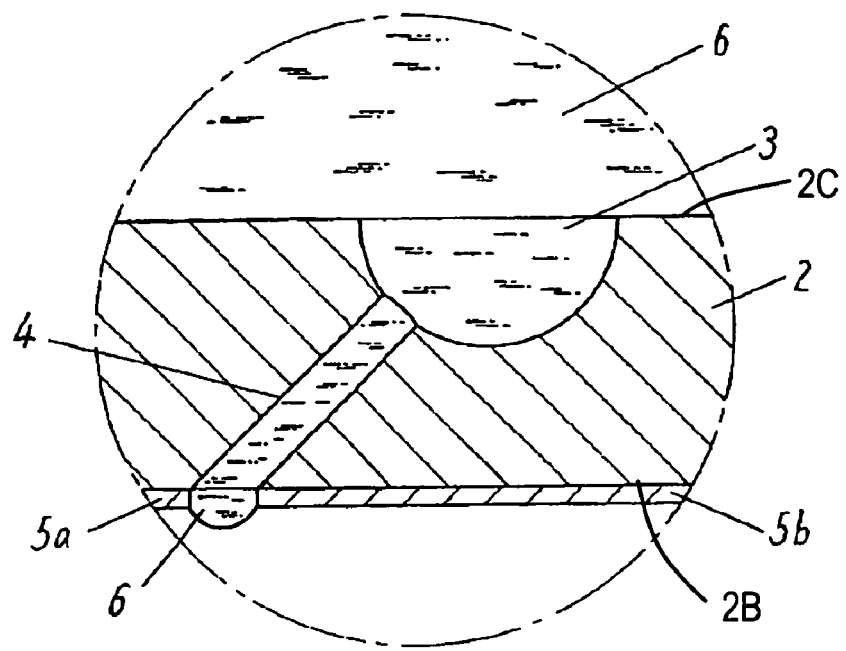
FIG. 7 is an enlarged cross sectional view of the essential part of the extracellular potential measuring device according to Embodiment 1.

First, a procedure of detecting physicochemical changes in a culture solution will be described. FIG. 6 and FIG. 7 are enlarged cross sectional views of pocket 3 and through-hole 4 formed in plate portion 2, and detector electrodes 5a and 5b. As shown in FIG. 7, culture solution 6, electrolyte substance, is applied on upper surface 2C of plate portion 2, and pocket 3 and through-hole 4 is filled with culture solution 6 in this order. When space 6 above upper surface 2C of plate portion 2 is pressurized, or a space under lower surface 2B of plate portion 2 is depressurized, culture solution 6 spouts out of through-hole 4. At this moment, a pressure for the pressuring or depressurizing may be determined to be an appropriate value as to allow culture solution 6 to form a meniscus shape at the opening at the tip of through-hole 4 stably.

Consequently, culture solution 6 stably contact detector electrodes 5a and 5b. As shown in FIG. 5, detector electrodes 5a and 5b are electrically isolated from each other. When culture solution 6 forms the meniscus shape at through-hole 4 and contacts detector electrodes 6a and 5b, detector electrodes 5a and 5b are electrically connected with each other via culture solution 6, which is electrolyte.

A resistance between detector electrode 5a and detector electrode 5b relates to an ion concentration of culture solution 6, so that changes in the ion concentration of culture solution 6 can be detected from changes in the resistance between electrode 5a and electrode 5b. When the meniscus shape of culture solution 6 is not completed, the detector electrodes are not well connected with each other, thereby exhibiting the resistance between the electrodes. Thus, this resistance indicates whether or not culture solution 6 forms an appropriate meniscus shape at through-hole 4.

A procedure of measuring extracellular potentials of a cell to be examined or physicochemical changes in the cell will be described.

Figure 8:
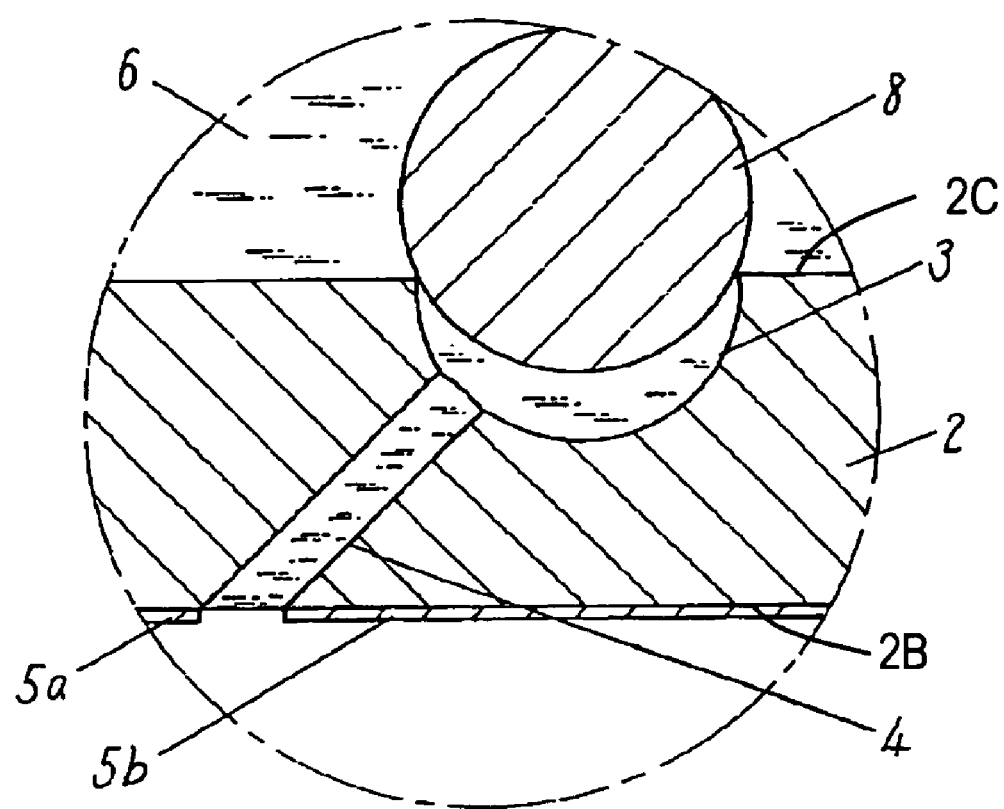
FIG. 8 is an enlarged cross sectional view of the essential part of the extracellular potential measuring device according to Embodiment 1.
Figure 9A:
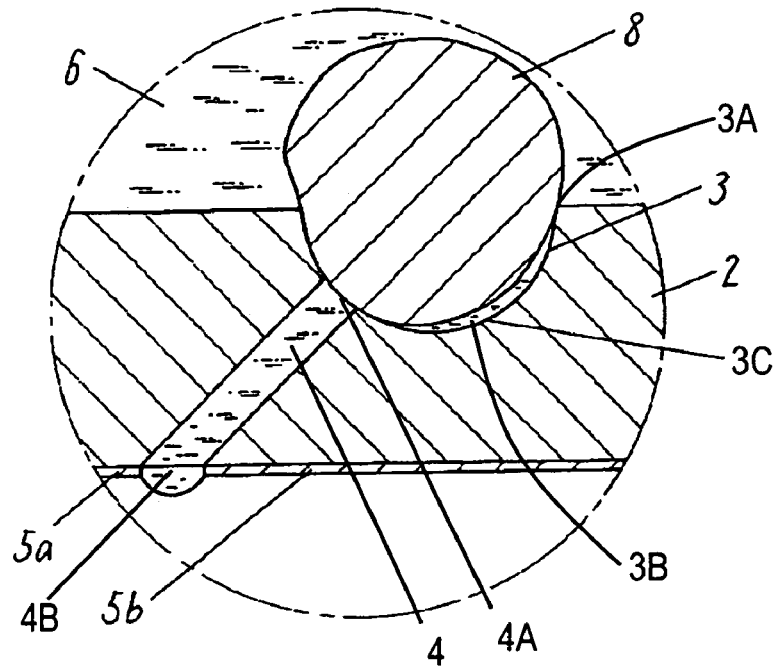
FIG. 9A is an enlarged cross sectional view of the essential part of the extracellular potential measuring device according to Embodiment 1.

As shown in FIG. 8, when cell 8 to be examined is put into pocket 3 with culture solution 6. Then, the space above upper surface 2C of plate portion 2 is pressurized, or the space under surface 2B of plate portion 2 is depressurized, and cell 8 is pulled into pocket 3 together with culture solution 6. As shown in FIG. 9A, cell 8 is further pulled towards through-hole 4, thereby having a cell membrane of cell 8 close opening 4A of through-hole 4 opening to pocket 3. Opening 4A of through-hole 4 is formed at a position closer to opening 3A than deepest point 3B of pocket 3. Therefore, when cell 8 is slightly larger than the diameter of opening 3A, clearance 3C is formed near deepest point 3B as shown in FIG. 9A, while cell 8 slightly deforms. Even in this case, however, cell 8 can still close opening 4A of through-hole 4. Thus, cell 8 can be held inside pocket 3 securely. The curved surface of pocket 3 holds cell 8 efficiently.

After cell 8 is held inside pocket 3, the pressure in the space above or under plate portion 2 can be controlled while measuring the resistance between detector electrodes 5a and 5b, so that culture solution 6 can form an appropriate meniscus shape at opening 4B of through-hole 4.

After cell 8 is held inside pocket 3 as to close opening 4A, stimulus is applied to cell 8. The stimulus may be not only chemical stimulus, such as chemical agents and poisons, but also physical stimulus, such as mechanical displacement, light, heat, electricity and electromagnetic wave. Upon reacting with the stimulus, cell 8 desorbs or absorbs various kinds of ions through the ion channels of the cell membrane. Such reaction occurs at a region where cell 8 contacts culture solution 6, and ion exchange also occurs between cell 8 and culture solution 6 inside through-hole 4. This changes the ion concentration of culture solution 6 in through-hole 4, and as described above, the change of the ion concentration can be detected via the resistance between detector electrodes 5a and 5b.

Figure 4:
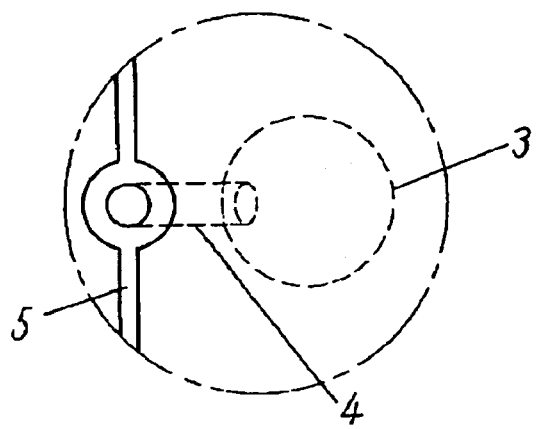
FIG. 4 is an enlarged view of an essential part of the extracellular potential measuring device according to Embodiment 1.
Figure 9B:
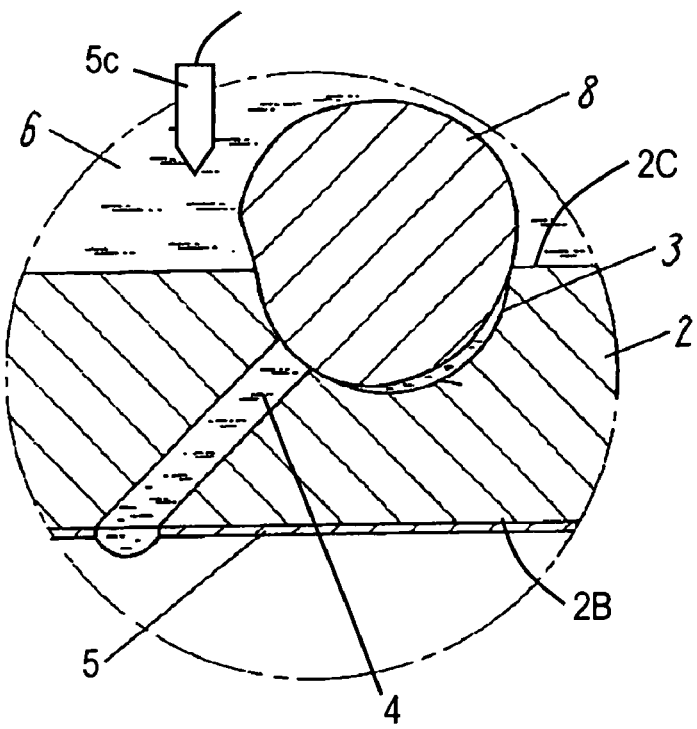
FIG. 9B is an enlarged cross sectional view of the essential part of the extracellular potential measuring device according to Embodiment 1.

In the aforementioned description, two detector electrodes 5a and 5b are provided. However, the measurement may be performed with a single detector electrode. Electrodes 5a and 5b shown in FIG. 5 are replaced by detector electrode 5 shown in FIG. 4 which is made essentially of gold and provided at a circumference of the opening of through-hole 4 on surface 2B of plate portion 2 towards on recess 1A. In this case, as shown in FIG. 9B, a voltage between detector electrode 5 and reference electrode 5C having the same potential as culture solution 6 filled on upper surface 2C of plate portion 2 is measured, and allows changes in the ion concentration inside through-hole 4 to be determined, hence allowing extracellular potentials of cell 8 or physicochemical changes in cell 8 to be detected.

The changes of the ion concentration may be determined by measuring not only the resistance but also other physical amounts, such as a current, a charge amount, and a potential.

Figure 10:
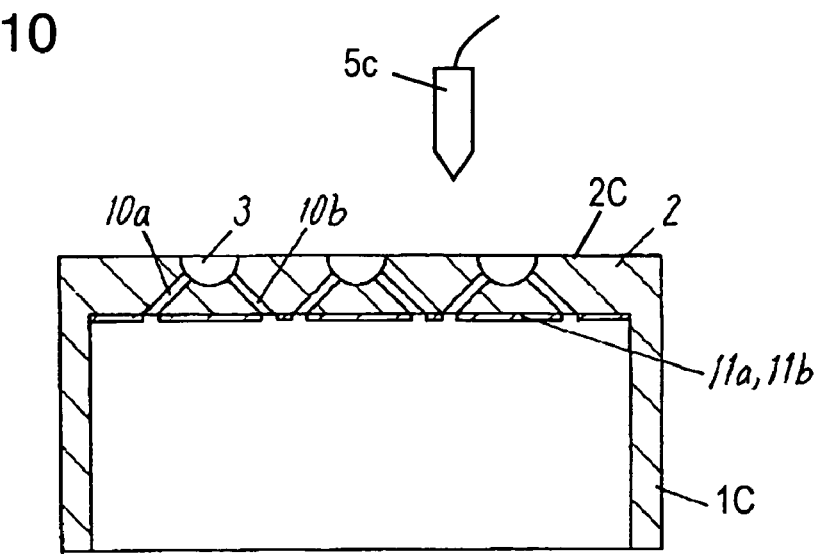
FIG. 10 is a cross sectional view of another extracellular potential measuring device according to Embodiment 1.
Figure 11:
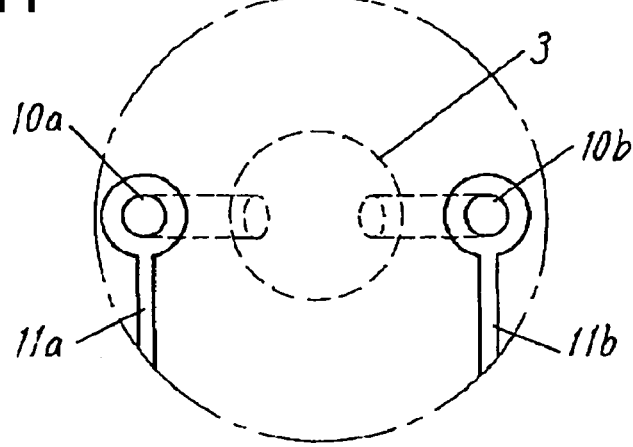
FIG. 11 is an enlarged cross sectional view of an essential part of the extracellular potential measuring device according to Embodiment 1.

FIG. 10 is a cross sectional view of another extracellular potential measuring device 52 according to Embodiment 1. In device 51 shown in FIG. 3, through-hole 4 is formed at the position closer to opening 3A than deepest point 3B of pocket 3 and inclines at 45° with respect to thickness direction 2A of plate portion 2. In device 52 according to Embodiment 1 shown in FIG. 10, through-holes 10a and 10b are extended from pocket 3 to lower surface 2B of plate portion 2. In device 52, as shown in FIG. 11, detector electrodes 11a and 11b mainly made of gold are provided inside through-holes 10a and 10b, respectively. Since through-holes 10a and 10b are provided separately from each other in device 52, detector electrodes 11a and 11b can be formed easily.

Culture solution 6 is applied onto upper surface 2C of plate portion 2, and pocket 3 and through-holes 10a and 10b is filled with culture solution 6. A difference between respective pressures at spaces above and under plate portion 2 makes culture solution 6 form meniscus shapes at the tips of through-holes 10a and 10b, thereby allowing the meniscus shapes to contact detector electrodes 11a and 11b, respectively. A resistance between detector electrodes 11a and 11b can determine whether appropriate meniscus shapes are formed at the tips of through-holes 10a and 10b or not, and detects the change of the ion concentration inside through-holes 10a and 10b.

The resistance between detector electrodes 11a and 11b is measured after cell 8 is put into pocket 3 with culture solution 6, and it can be determined whether cell 8 held in pocket 3 so that the cell membrane covers through-holes 10a and 10b. If the cell membrane closes only through-hole 10a and does not closes through-hole 10b, the resistance between detector electrode 11a and reference electrode 52c contacting culture solution 6 over plate portion 2 is large, and the resistance between detector electrode 11b and reference electrode 52c is small. In this case, the resistance between reference electrode 52c and detector electrode 11a can be measured to determine activities of cell 8 which will be described later. In the contrary, in the case that cell 8 closes through-hole 11b and does not close through-hole 11a, the resistance between reference electrode 52c and detector electrode 11b can be measured to determine activities of cell 8. Thus, the activities of cell 8 can be measured as long as the cell membrane of cell 8 covers either one of through-holes 10a and 10b. This structure increases the possibility of measuring the activities, thereby improving reliability of the device.

If cell 8 held is subjected to an external stimulus while the cell membrane covers through-holes 10a and 10b, then cell 8 is activated, and the ion concentrations inside through-holes 10a and 10b change, thereby allowing extracellular potentials of cell 8 or physicochemical changes in cell 8 to be detected.

In devices 51 and 52 shown in FIGS. 3 and 10, through-holes 4 and 10a, 10b are formed at the positions closer to openings 3A than deepest point 3B of pocket 3. Alternatively, through-hole 14 may be easily formed at deepest point 3B, as shown in FIG. 21. In this case, however, the diameter and shape of pocket 3 is adjusted in accordance with the shape of cell 8 so as to facilitate for cells 8 to reach deepest points 3B.

The cross sections of through-holes 4, 10a, and 10b have the circular or oval shapes according to Embodiment 1, and may have rectangular shapes or U-shapes.

FIGS. 22 and 23 are perspective views of extracellular potential measuring device having through-holes 15 and 17 having cross sections having the rectangular and U-shape, respectively. Through-hole 15 having the rectangular cross section, as shown in FIG. 22, provides pocket 16 with a semi-cylindrical shape with round corners. Through-hole 17 having a U-shape cross section, as shown in FIG. 23, provides pockets 18 with a substantially-semispherical shape.

Pocket 16 having the semi-cylindrical shape is suitable to cell 8 having a long and narrow fixed shape (e.g. a ganglion cell extracted from *Lymnaea stagnalis*).

A combination of pocket 18 having the semispherical shape and through-hole 17 having the U-shape cross section is effective for measuring cell 8 which easily deforms. Cell 8 which easily deforms may pass through through-hole 4 having a circular cross section. Through-hole 17 having the U-shape cross section, on the other hand, the minimum width of opening 17A of through-hole 17 that opens to pocket 18 is reduced without an decrease of culture solution 6 to fill into through-hole 17 having the U-shape cross section. This can prevent cell 8 from falling into through-hole 17 and being damaged. The cross section of through-hole 17 may have can be a combination of plural U-shapes, a combination of plural rectangular shapes, or a combination of the U-shape and the rectangular shape.

The diameters of pockets 3, 16 and 18 and the diameters of through-holes 4, 15 and 17 are determined in accordance with the size, shape, and properties of cell 8. Cell 8 having a diameter ranging from 5 to 100 μm can be measured with pockets 3, 16 and 18 having diameters ranging from 10 to 100 μm, and through-holes 4, 15, and 17 having diameters ranging from 1 to 10 μm.

A method for manufacturing extracellular potential measuring device 51 according to Embodiment 1 will be described. FIG. 12 to FIG. 21 are cross sectional views of extracellular potential measuring device 51 for illustrating the method for manufacturing the device according to Embodiment 1.

Figure 12:
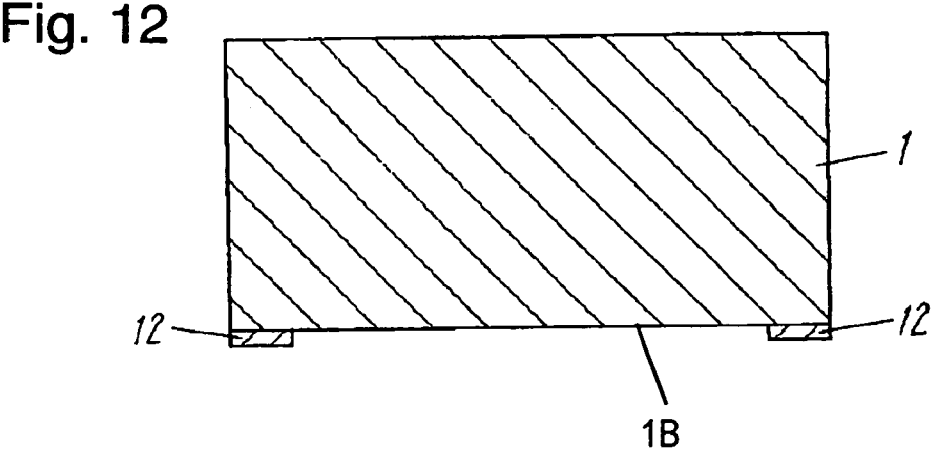
FIG. 12 is a cross sectional view of the extracellular potential measuring device for illustrating a method for manufacturing the device according to Embodiment 1.
Figure 13:
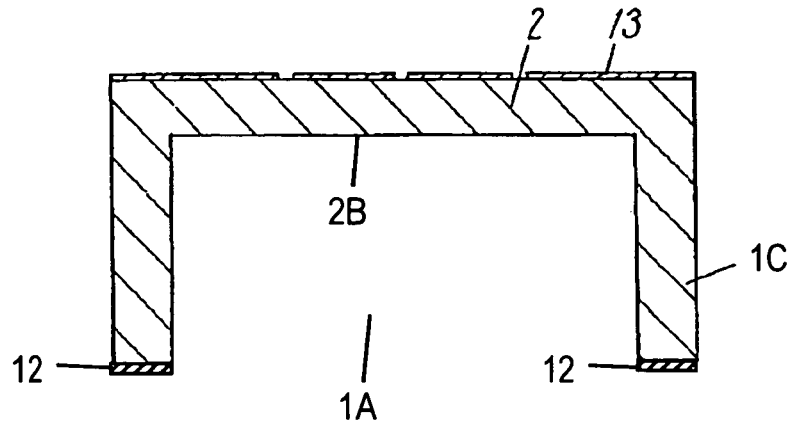
FIG. 13 is a cross sectional view of the extracellular potential measuring device for illustrating a method for manufacturing the device according to Embodiment 1.

Resist mask 12 is provided on lower surface 1B of substrate 1 made of silicon, as shown in FIG. 12. Then, substrate 1 is etched by a prescribed depth from lower surface 1B so as to form recess 1A and lower surface 2B of plate portion 2, as shown in FIG. 13. Plate portion 2 is supported by ridge 1C of substrate 1. Resist mask 12 is than removed.

Figure 14:
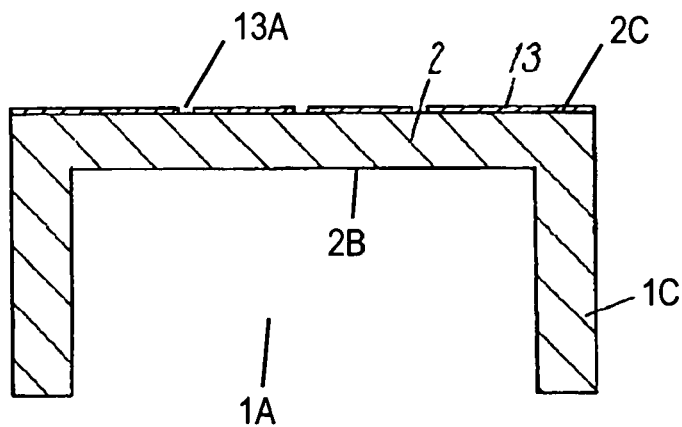
FIG. 14 is a cross sectional view of the extracellular potential measuring device for illustrating a method for manufacturing the device according to Embodiment 1.

Next, as shown in FIG. 14, resist mask 13 is provided on upper surface 2C of plate portion 2. Resist mask 13 has etching holes 13A having cross sections of shapes substantially identical to predetermined shapes of through-holes 4.

Figure 15:
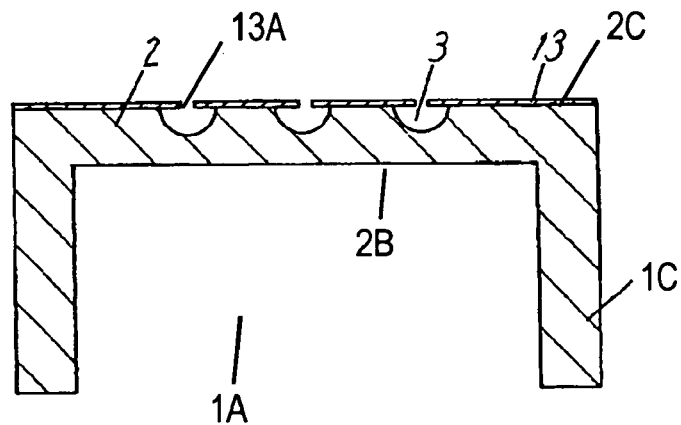
FIG. 15 is a cross sectional view of the extracellular potential measuring device for illustrating a method for manufacturing the device according to Embodiment 1.

Then, as shown in FIG. 15, plate portion 2 is etched from upper surface 2C with gas for accelerating etching. Substrate 1 made of silicon can be etched with $SF_6$, $CF_4$, $XeF_2$ as the gas for accelerating etching. These gases accelerate the etching not only in the depth direction of substrate 1, that is, in a direction orthogonal to mask 13, but also in the lateral direction, that is, in a direction parallel to mask 13. Consequently, as shown in FIG. 15, an etched portion has a semi-sphere shape as its center at openings 13A of mask 13, thereby providing pocket 3.

Figure 16A:
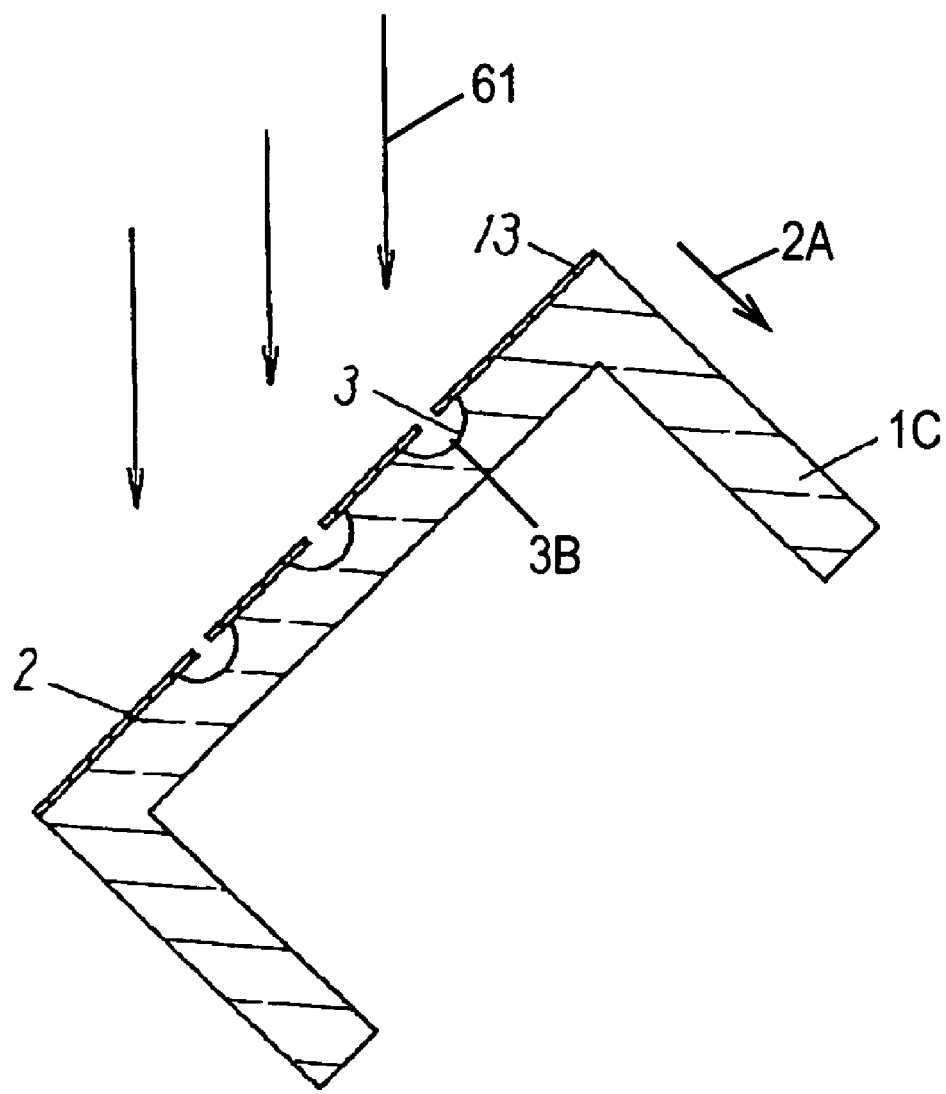
FIG. 16A is a cross sectional view of the extracellular potential measuring device for illustrating a method for manufacturing the device according to Embodiment 1.

Then, as shown in FIG. 16A, substrate 1 is dry-etched while substrate 1 inclines at 45° with respect to direction 61 in which ions of etching gas flow. As the etching gas, the gas for accelerating etching and gas for suppressing the etching are used alternately. The gas for accelerating the etching may be $XeF_2$, $CF_4$, $SF_6$. The gas for suppressing the etching may be $CHF_3$, $C_4F_8$. Substrate 1 is etched with the gas for suppressing the etching to have protective film 31 of $CF_2$ polymer on an etched wall, as shown in FIG. 16C, so that the dry etching proceeds only in direction 61 from etching hole 13A, thereby forming through-hole 4 extending in direction 61.

The etching proceeding only in direction 61 from etching hole 13A will be described in detail.

Figure 16B:
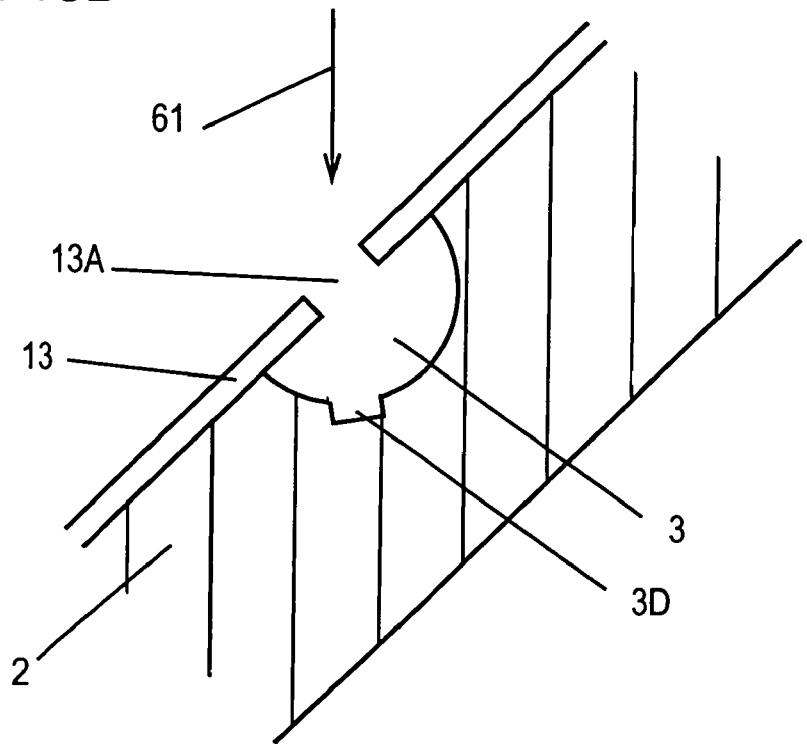
FIG. 16B is a cross sectional view of the extracellular potential measuring device for illustrating a method for manufacturing the device according to Embodiment 1.

First, substrate 1 is etched a little with the gas for accelerating the etching, as shown in FIG. 16B. In this process, a high frequency is applied to substrate 1 in plasma generated by an inductive coupling method with an external coil. Consequently, a minus bias voltage generated on substrate 1 makes plus ions $SF_5^+$ or $CF_3^+$ in the plasma of the etching gas collide against substrate 1, whereby substrate 1 is dry-etched in predetermined direction 61 precedence over the other directions. However, there are some plus ions that proceed in a direction different from direction 61, so that hole 3D having a diameter slightly larger than that of etching hole 13A is formed in plate portion 2.

Figure 16C:
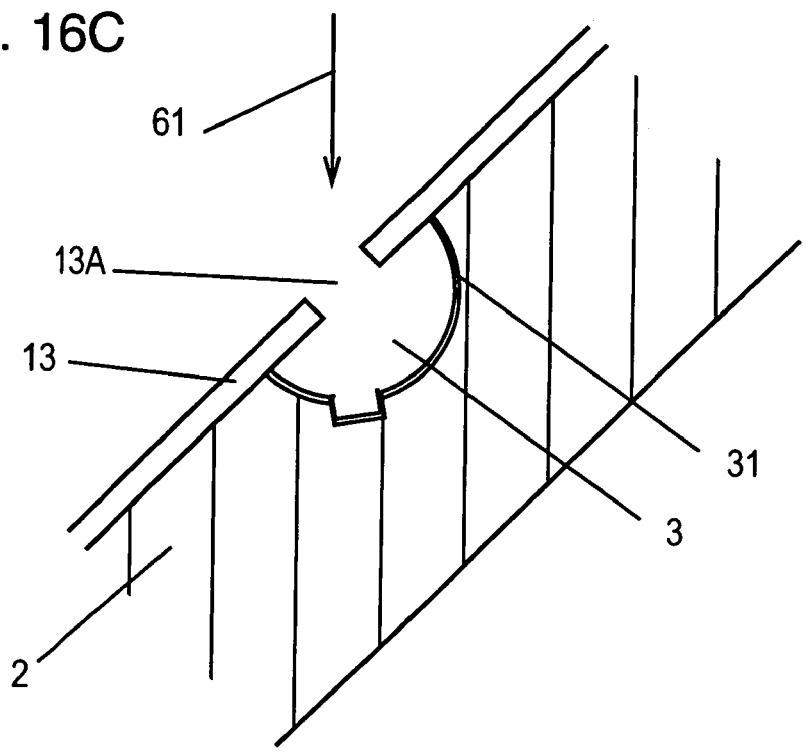
FIG. 16C is a cross sectional view of the extracellular potential measuring device for illustrating a method for manufacturing the device according to Embodiment 1.

Then, protective film 31 is formed on the etched portion of substrate 1, as shown in FIG. 16C. In this process, no high frequency is applied to substrate 1. As a result, no bias voltage is generated on substrate 1, so that $CF^+$, material of protective film 31, does not deflect, thereby forming uniformly protective film 31 on the wall of the etched portion of substrate 1.

Figure 16D:
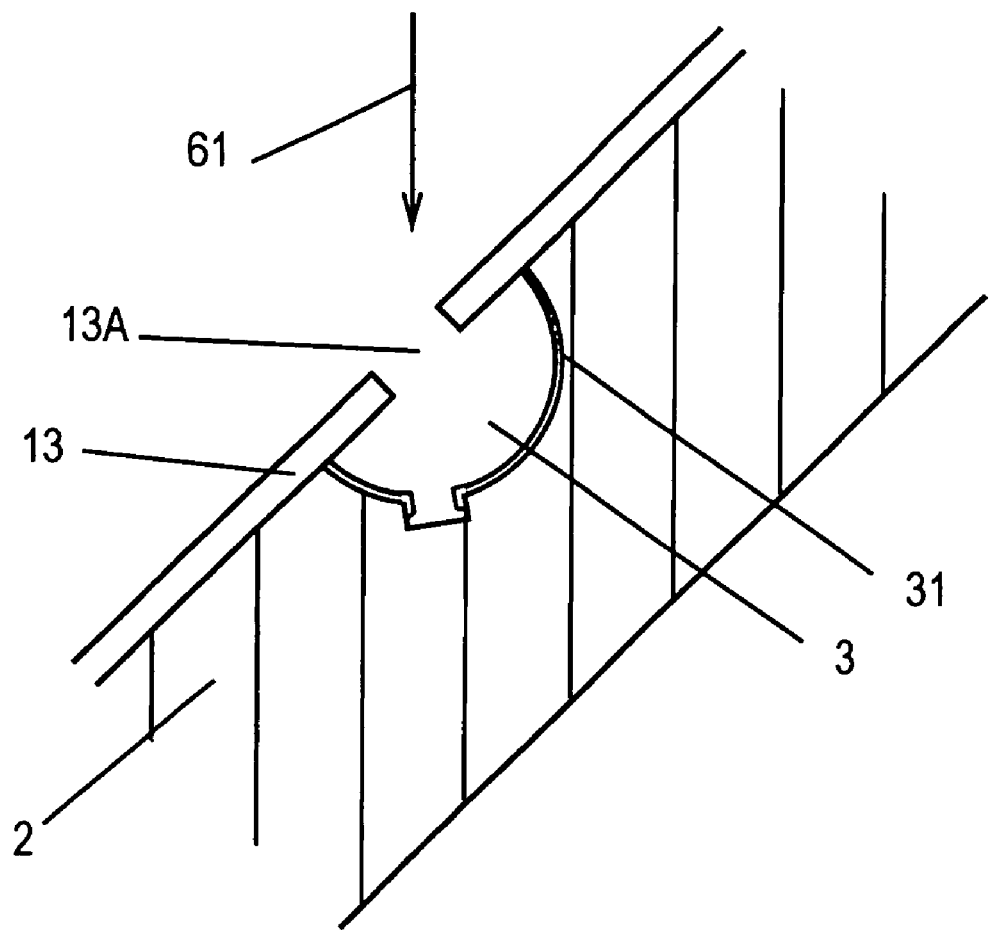
FIG. 16D is a cross sectional view of the extracellular potential measuring device for illustrating a method for manufacturing the device according to Embodiment 1.

Next, substrate 1 is etched a little again with the gas for accelerating etching, as shown in FIG. 16D. In this process, a high frequency is applied again to substrate 1. This biases substrate 1, thereby allowing more ions of the etching gas to flow in parallel to direction 61. These ions have high energy, and etches protective film 31 on the lower surface of the etched portion. However, ions moving in the directions not parallel to direction 61 have too low energy to easily remove protective film 31 formed on the wall. The etching alternately using the gas for accelerating the etching and the etching with the gas for suppressing the etching proceeds only in direction 61 from etching hole 13A, thereby forming through-hole 4 extending in direction 61 from etching hole 13A. This method provides the wall of through-hole 4 with a difference in level, as shown in FIG. 16D. However, this difference is smaller than the diameter of through-hole 4 and is substantially ignorable, so that through-hole 4 extends substantially in direction 61.

Figure 17:
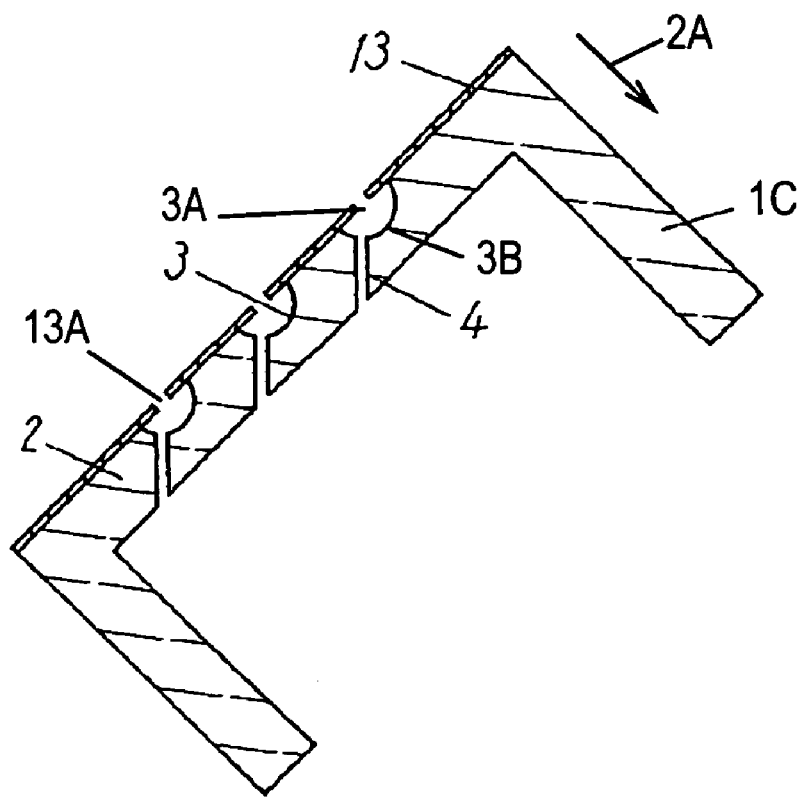
FIG. 17 is a cross sectional view of the extracellular potential measuring device for illustrating a method for manufacturing the device according to Embodiment 1.

In this process, the etching proceeds from etching holes 13A only in direction 61 in which gas ions flow, so that, as shown in FIG. 17, through-hole 4 is formed at the position closer to opening 3A than deepest point 3B of pocket 3 and inclines at 45° with respect to thickness direction 2A of plate portion 2. Since substrate 1 inclining is etched, through-hole 4 has a cross section having a shape different from that of etching hole 13A of resist mask 13. Etching hole 13A has an oval shape having a long diameter in the direction to which substrate 1 inclines, and through-holes 4 can have a circular cross section.

The angle of the inclining of substrate 1 is limited according to the shape of etching hole 13A and the thickness of resist mask 13. For example, when etching holes 13A has a diameter of 1 µm and resist mask 13 has a thickness of 1 µm, direction 61 preferably inclines at an angle smaller than 45° with respect to thickness direction 2A of plate portion 2 due to geometrical limitations. Otherwise, substrate 1 cannot be etched.

When substrate 1 is etched while not inclining, as shown in FIG. 21, through-hole 14 is formed at deepest point 3B of pocket 3. If cell 8 has a size large enough to reach deepest point 3B of pocket 3, through-holes 14 may be formed in the position shown in FIG. 21.

Etching hole 13A of resist mask 13 may have a rectangular shape, a U-shape, or a combination of the shapes besides the aforementioned circular or oval shape.

Etching holes 13A having the rectangular shape provides substantially semi-cylindrical pocket 16 with round upper and lower surfaces, as shown in FIG. 22, with the gas for accelerating the etching, and through-hole 15 has a rectangular cross section having a shape identical to that of etching hole 13A. Since the long side of the rectangle is larger than the diameter of the circle, plural detector electrodes can be easily formed in each through-hole.

Etching hole 13A having a U-shape cross section, the gas for accelerating the etching etches substrate 1 in all directions from hole 13A, and provides semispherical pocket 18, as shown in FIG. 23. Similarly to through-hole 4 shown in FIG. 3, through-hole 17 has a U-shape cross section having a shape identical to the shape of etching hole 13A.

In the case that plural through-holes are formed in each pocket 3, as shown in FIG. 10 and FIG. 11, while through-holes 4 are formed, substrate 1 is etched while changing the angle of its inclination. Resist mask 13 is removed after the etching.

Figure 18:
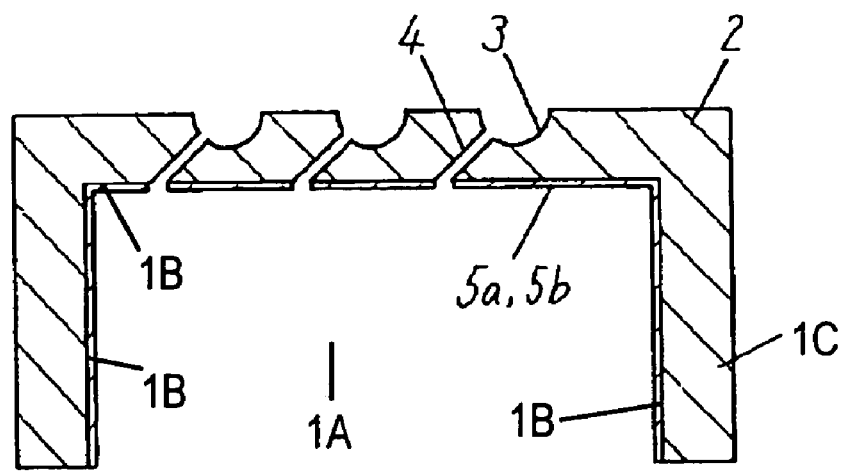
FIG. 18 is a cross sectional view of the extracellular potential measuring device for illustrating a method for manufacturing the device according to Embodiment 1.
Figure 19:
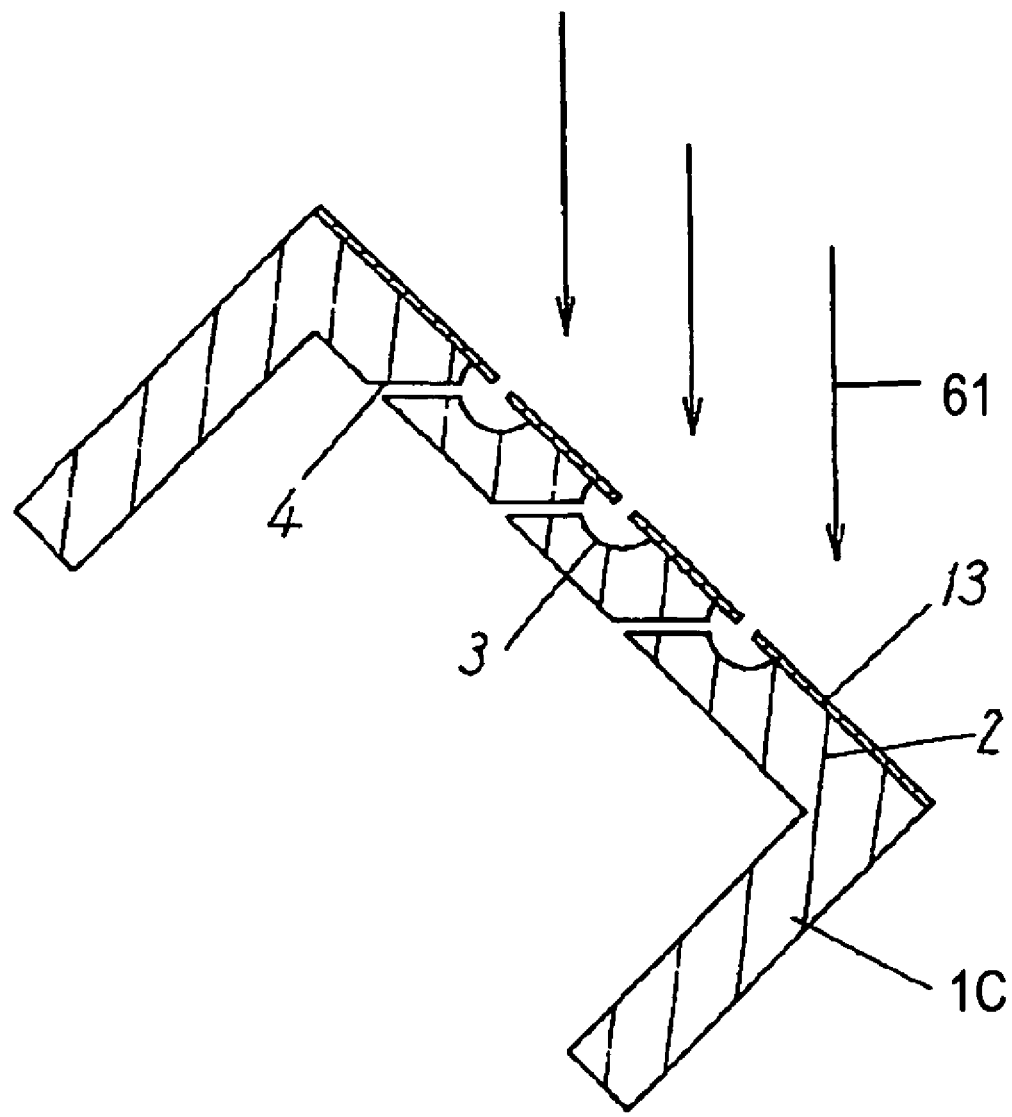
FIG. 19 is a cross sectional view of the extracellular potential measuring device for illustrating a method for manufacturing the device according to Embodiment 1.

Next, as shown in FIG. 18, detector electrodes 5a and 5b made essentially of gold are formed near through-holes 4 by a method of forming a thin film onto surface 1B of substrate 1 towards recess 1A. Although surface 1B of substrate 1 has asperities, it is possible to apply coating, exposing and patterning of a photo resist to such a rough surface. However, if extremely precise electrodes are necessary, pockets 3 may be formed on surface 62B of plate portion 2 towards recess 1A after the formation of plate portion 2 onto substrate 1, as shown in FIG. 20. Surface 62C can be processed more precisely than surface 62B by a mechanical or chemical method. This method facilitates the manufacture of the device since detector electrodes 5a and 5b require high precision, while pocket 3 can be generally made at precision less than detector electrodes 5a and 5b.

As shown in FIG. 10, if each pocket 3 has two through-holes 10a and 10b, detector electrodes 11a and 11b are formed, as shown in FIG. 11, in an ordinary process for forming a thin film as described above. In this case, electrodes 11a and 11b can be formed more easily than electrodes 5a and 5b since electrodes 11a and 11b may not be as precise as electrodes 5a and 5b which are formed in the device having a single through-hole 4 linked with single pocket 3, as shown in FIG. 3.

According to Embodiment 1, pockets 3 and through-holes 4 are formed after substrate 1 has recess 1A, lower surface 2B of plate portion 2 and has ridge 1C supporting plate portion 2. However, an extracellular potential measuring device having the same structure may be obtained by forming pockets 3 and through-holes 4 before substrate 1 has recess 1A, lower surface 2B of plate portion 2, and has ridge 1C supporting plate portion 2.

Figure 24:
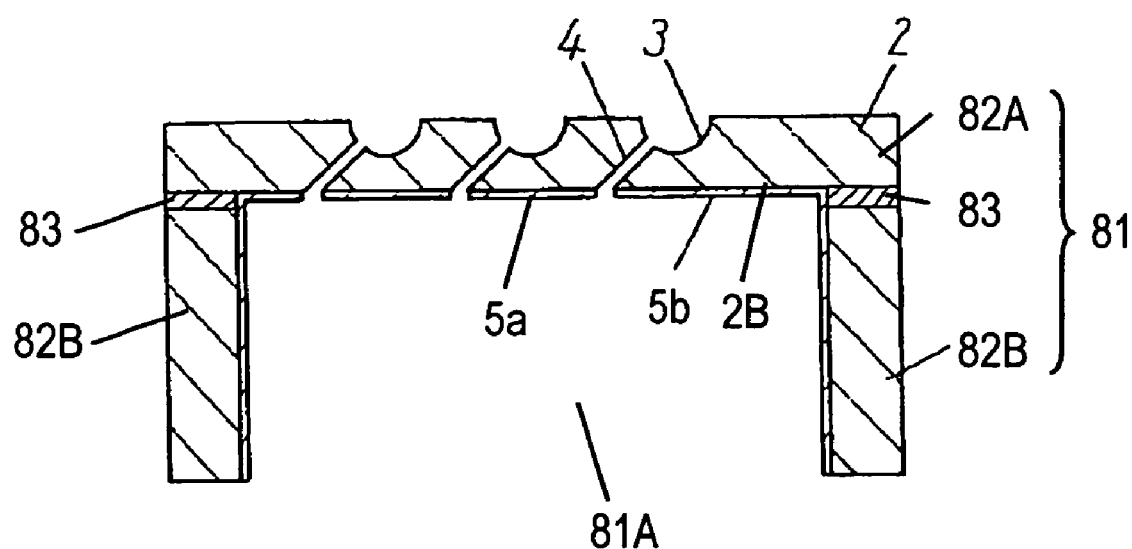
FIG. 24 is a cross sectional view of a further extracellular potential measuring device according to Embodiment 1.

FIG. 24 is a cross sectional view of a further extracellular potential measuring device according to Embodiment 1. In the extracellular potential measuring devices shown in FIGS. 1 to 23, substrate 1 employs a silicon substrate. However, the extracellular potential measuring device may include, instead of substrate 1 made of silicon, SOI substrate 81 including silicon layer 82A to serve as plate portion 2, silicon oxide layer 83, and silicon layer 82. Oxide silicon layer 83 is provided at a rim of lower surface 2B of plate portion 2, and silicon layer 82B is provided on silicon oxide layer 83. In SOI substrate 81, etching terminates at silicon oxide layer 83, thereby providing through-holes 4 and plate portion 2 having a precise thickness in either case of forming ridge 81A in substrate 81 or through-holes in plate portion 2 by etching.

Exemplary Embodiment 2

Figure 25:
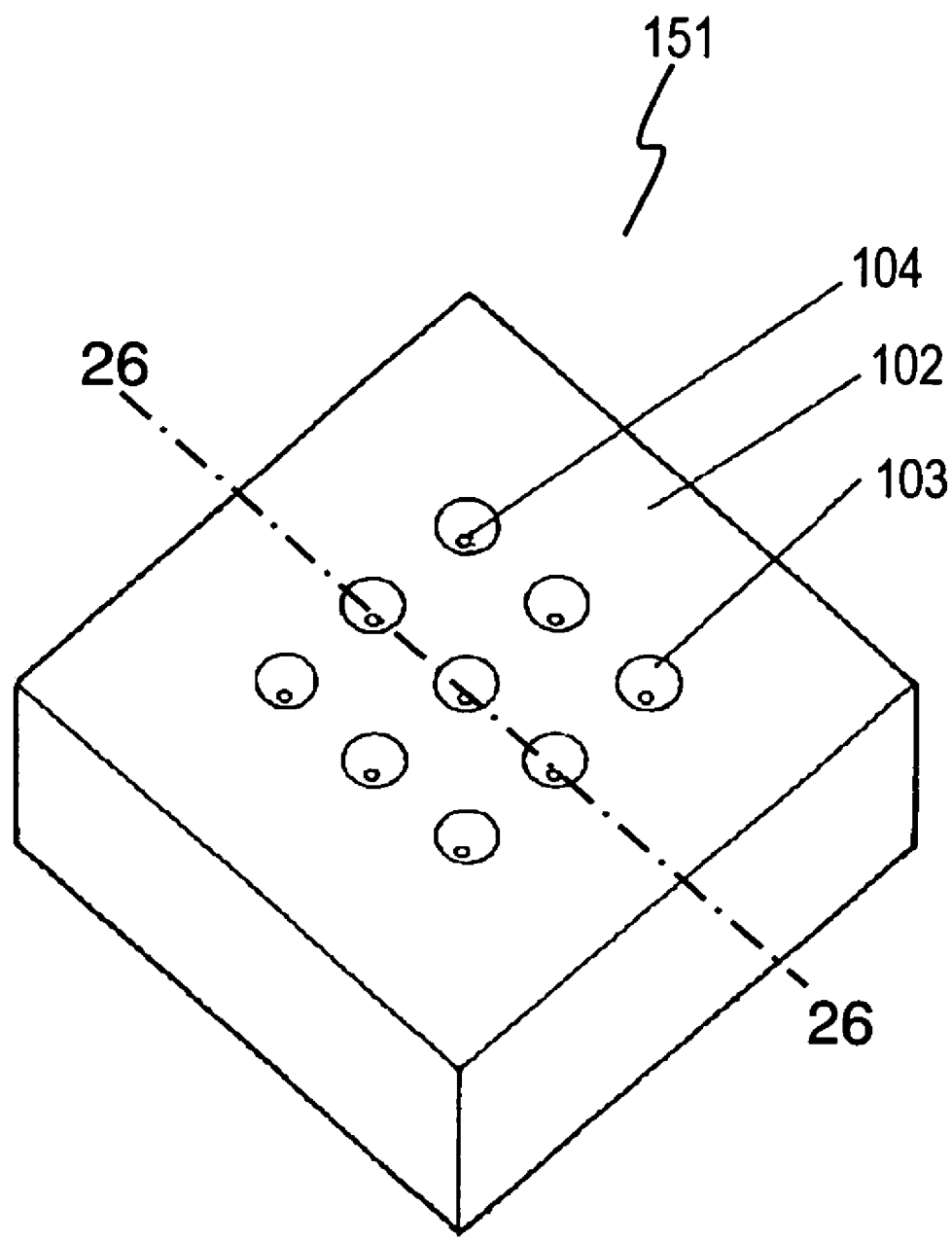
FIG. 25 is a perspective view of an extracellular potential measuring device according to Exemplary Embodiment 2 of the invention.
Figure 26:
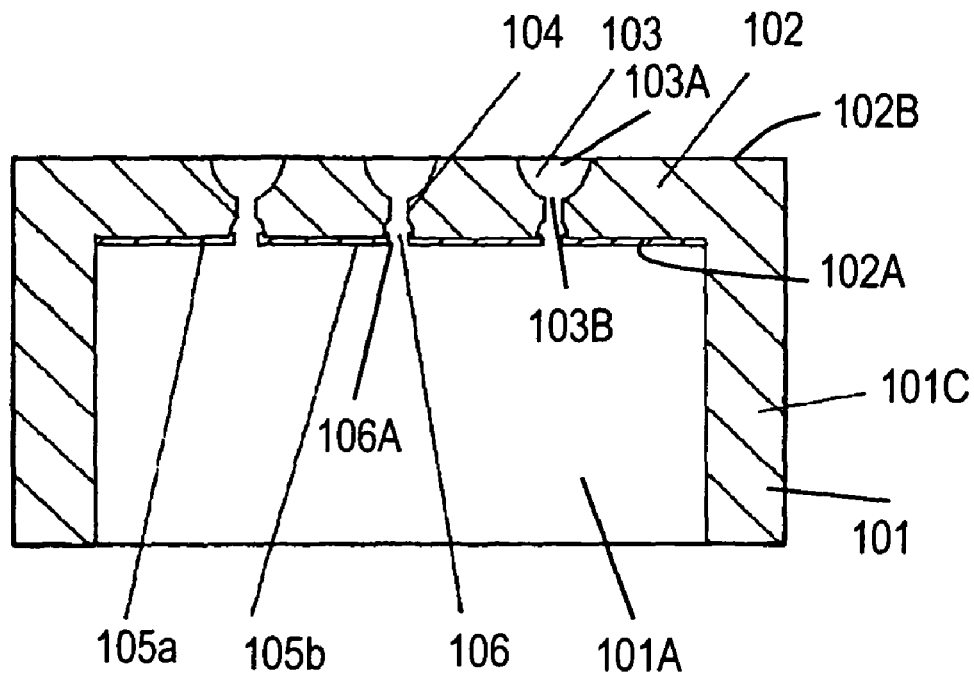
FIG. 26 is a cross sectional view of the extracellular potential measuring device according to Embodiment 2.
Figure 27:
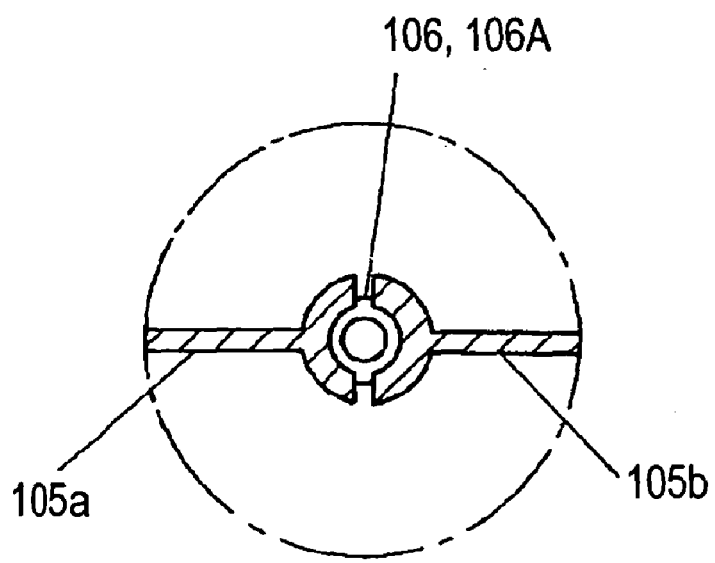
FIG. 27 is an enlarged view of an essential part of the extracellular potential measuring device according to Embodiment 2.

FIG. 25 is a perspective view of extracellular potential measuring device 151 according to Exemplary Embodiment 2 of the present invention. FIG. 26 is a cross sectional view of device 151 taken along line 26-26 shown in FIG. 25. FIG. 27 is an enlarged view of an essential part of device 151.

As shown in FIGS. 25 to 27, substrate 101 made of silicon has recess 101A having lower surface 102A providing plate portion 102 is formed. Substrate 101 has ridge 101C supporting plate portion 102. Plate portion 102 is made of silicon similarly to substrate 101, and has a thickness of about 25 μm. Pocket 103 has a semispherical surface and opening 103A having a diameter of about 20 μm and opening in a surface of substrate 101. Pocket 103 communicates with through-hole 104. Through-hole 104 has a uniform cross section along its whole length in its longitudinal direction and pass through plate portion 102. Through-hole 4 is provided at deepest portion 103B of pocket 103, and has a circular cross section having a diameter of about 5 μm or an oval cross section having a long diameter of about 5 μm.

Pocket 106 flaring towards surface 102B is provided at an end of through-hole 104 opposite to pocket 103. Detector electrodes 105a and 105b mainly made of gold are formed around opening 106A of pocket 106 on lower surface 102A of plate portion 102 at a side to recess 1A.

Figure 28A:
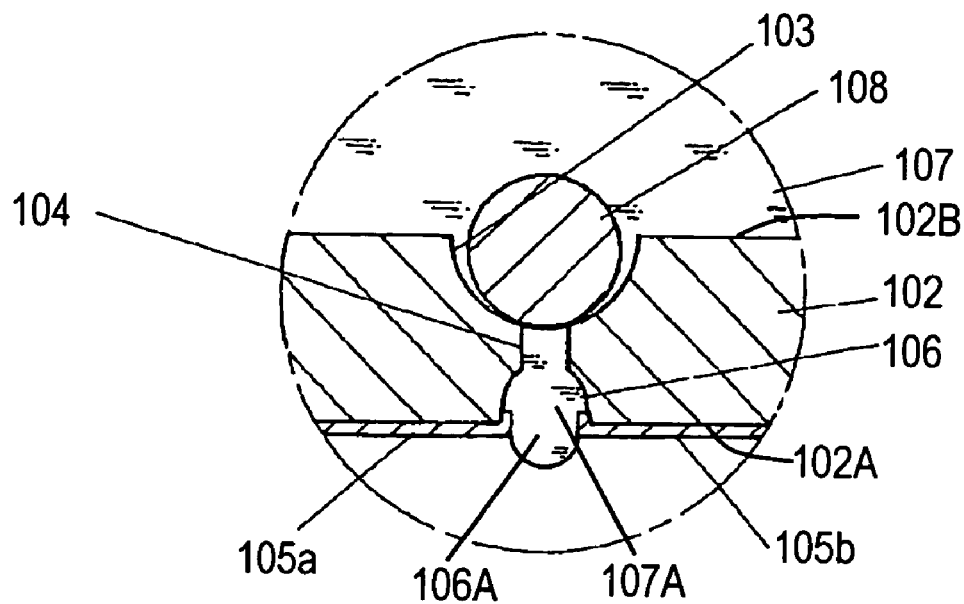
FIG. 28A is an enlarged cross sectional view of the extracellular potential measuring device for illustrating an operation of the device according to Embodiment 2.

An operation of extracellular potential measuring device 151 will be described. FIG. 28A is an enlarged cross sectional view of an essential part of device 151.

First, a procedure of detecting physicochemical changes in a culture solution will be described. As shown in FIG. 28A, culture solution 107, electrolyte fills over upper surface 102B of plate portion 102 opposite to lower surface 102A, and pocket 103 and through-hole 104 are filled with culture solution 107 in this order. When a space over upper surface 102B of plate portion 102 is pressurized, or when a space under lower surface 102A of plate portion 102 is depressurized, culture solution 107 spouts out of through-hole 104. Upon the pressure of the pressuring or depressurizing being adjusted appropriately, culture solution 107 forms a meniscus at opening 106A of pocket 106 and keeps it stably.

Consequently, culture solution 107 contacts detector electrodes 105a and 105b stably. Detector electrodes 105a and 105b are electrically isolated from each other. However, when culture solution 107 forms the meniscus at pocket 106 and contacts detector electrodes 105a and 105b, detector electrodes 105a and 105b are electrically connected with each other via culture solution 107, electrolyte.

A resistance between detector electrodes 105a and 105b relates to an ion concentration of culture solution 107, so that changes in the ion concentration of culture solution 107 can be detected from changes of the resistance between detector electrodes 105a and 105b. When the meniscus of culture solution 107 is imperfect, detector electrodes 105a and 105b are not sufficiently connected with each other, hence increasing the resistance. Thus, the measured resistance indicates whether or not culture solution 107 forms the meniscus appropriately at pocket 106.

Pocket 106 has a region extending from through-hole 4 to lower surface 102A of plate portion 102 not straight-lined but a combination of a straight surface and a curved surface of pocket 106, thereby providing a step surface. Such structure facilitates the formation of the meniscus of culture solution 107 inside pocket 106 after passing through through-hole 104. The step surface of pocket 106 increases a surface tension of culture solution 107, hence keeping a pressure balance regardless of a slight variation in vertical pressure difference. In other words, once the meniscus of culture solution 107 is formed, it is kept in pocket 106 even if there is a slight pressure fluctuation. This phenomenon was confirmed by a finite element method for fluid dynamics. The stable meniscus stabilize an amount of culture solution 107 inside through-hole 104 and pocket 106, hence allowing the ion concentration to be measured stably.

Detector electrodes 105a and 105b extend to pockets 106, as shown in FIG. 26, and are stably connected with culture solution 107 due to the meniscus of culture solution 107.

A procedure of measuring extracellular potentials of a cell to be examined or physicochemical changes in the cell will be described.

As shown in FIG. 28A, cell 108 to be examined is put in pocket 103 with culture solution 107, and then, a space over upper surface 102B of plate portion 102 is pressurized, or a space under lower surface 102A of plate portion 102 is depressurized. Then, cell 108 and culture solution 107 are pulled into pocket 103. A curved surface of pocket 103 holds cell 108 efficiently.

After cell 108 is held inside pocket 103, a vertical pressure of plate portion 102 is controlled so that culture solution 107 can form an appropriate meniscus at opening 106A of pocket 106. The pressure can be controlled while measuring the resistance between detector electrodes 105a and 105b as described above.

After cell 108 is held inside pocket 103 and closes an opening of through-hole 104, stimuli are applied to cell 108. The stimuli include not only chemical stimuli, such as chemical agents and poisons, but also physical stimuli, such as mechanical displacement, light, heat, electricity and electromagnetic wave.

Upon actively reacting with the stimuli, cell 108 desorbs or absorbs various kinds of ions through ion channels of a cell membrane of the cell. This reaction occurs at a region where cell 108 contacts culture solution 107, and ion exchange is performed in between a volume of culture solution 107A in through-hole 104 and pocket 106 and cell 108. This results in changes in the ion concentrations of the volume of culture solution 107A in through-hole 104 and pocket 106, so that the change of the ion concentration can be detected from detector electrodes 105a and 105b.

Figure 28B:
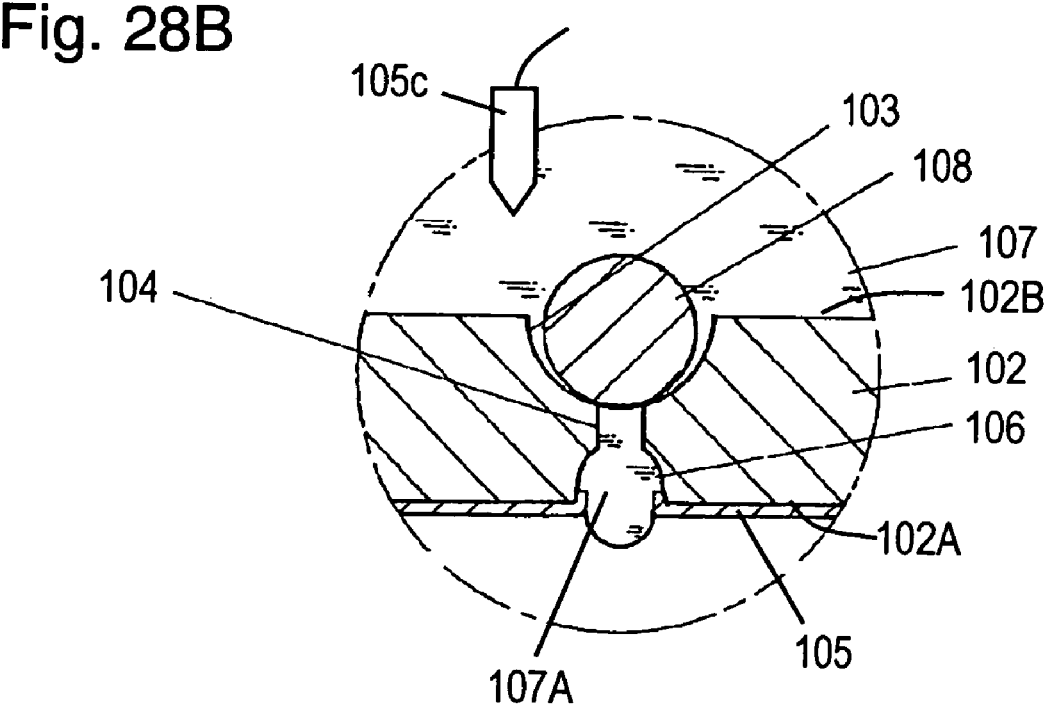
FIG. 28B is an enlarged cross sectional view of the extracellular potential measuring device for illustrating an operation of the device according to Embodiment 2.

In FIG. 28A, two detector electrodes 105a and 105b are used to measure the change; however, the change can be measured with a single detector electrode. FIG. 28B is an enlarged cross sectional view of an essential part for explaining an operation of extracellular potential measuring device 15 according to Embodiment 2. A voltage between reference electrode 105c having the same potential as culture solution 107 filling the space over upper surface 102B of plate portion 102 and single detector electrode 105 provided around pocket 106 is measured as to determine changes in the ion concentrations inside through-hole 104 and pocket 106, and hence allowing extracellular potentials of cell 108 or physicochemical changes in cell 108 to be measured.

The change in the ion concentration can be determined by measuring not only the resistance but also other physical quantity, such as a current, an amount of charge, and a potential.

Figure 35:
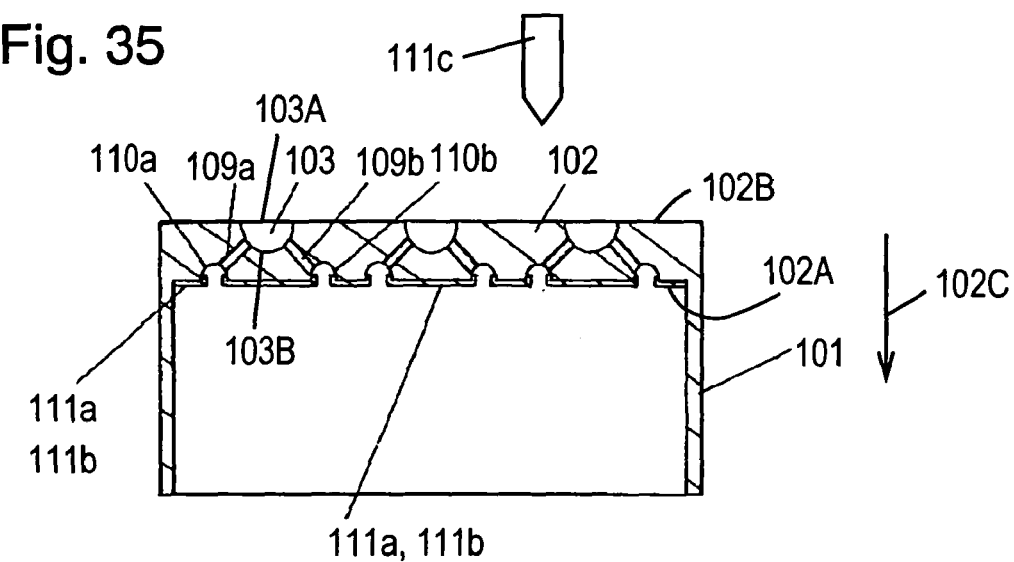
FIG. 35 is a cross sectional view of another extracellular potential measuring device according to Embodiment 2.
Figure 36:
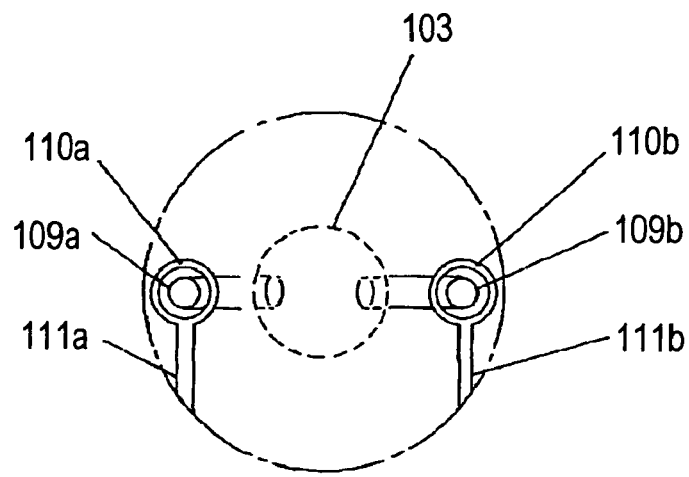
FIG. 36 is an enlarged cross sectional view of the extracellular potential measuring device shown in FIG. 35.

As shown in FIGS. 35 and 36, through-holes 109a and 109b are provided at a position closer to opening 103A than deepest portion 103B of pocket 103 and inclines at 45° with respect to thickness direction 102C of plate portion 102. Such structure enables plural through-holes 109a and 109b to extend from pockets 103, and provides pockets 110a and 110b at openings of through-holes 109a and 109b in plate portion 102 in such a manner that pockets 110a and 110b expand to lower surface 102A. As shown in FIG. 36, detector electrodes 111a and 111b mainly made of gold are provided inside pockets 110a and 110b, respectively. Since pockets 110a and 110b are provided separately from each other, detector electrodes 111a and 111b can be formed easily.

Culture solution 107 fills a space over upper surface 102B of plate portion 102, and pocket 103 and through-holes 109a, 109b are filled with culture solution 107A. A difference of pressures between above and under plate portion 102 makes culture solution 107A form meniscuses at ends of pockets 110a and 110b, thereby having the meniscuses contact detector electrodes 111a and 111b, respectively. The resistance value between detector electrodes 111a and 111b, upon being measured, can determine whether or not appropriate meniscuses are formed at the ends of pockets 110a and 110b, thereby allowing the ion concentration to change in through-holes 109a and 109b and pockets 110a and 110b.

When cell 108 (not illustrated) is put into pocket 3 together with culture solution 107, it can be determined whether or not cell 108 is held in pocket 3 as to have the cell membrane cover through-holes 109a and 109b. If the cell membrane closes only through-hole 109a and not through-hole 109b, the resistance between detector electrode 111a and reference electrode 111c contacting with culture solution 107 is large upon being measured from culture solution 107 over plate portion 102, and the resistance between detector electrode 111b and reference electrode 111c is small.

Under the aforementioned condition, if a stimulus is applied, cell 108 is activates, and the ion concentrations inside through-holes 109a and 109b and pockets 110a and 110b change, thereby enabling extracellular potentials of cell 108 or physicochemical changes in cell 108 to be detected.

Pocket 103 can have an appropriate diameter and a shape according to cells 108 so as to facilitate for cell 108 to reach deepest portion 103B.

Figure 41:
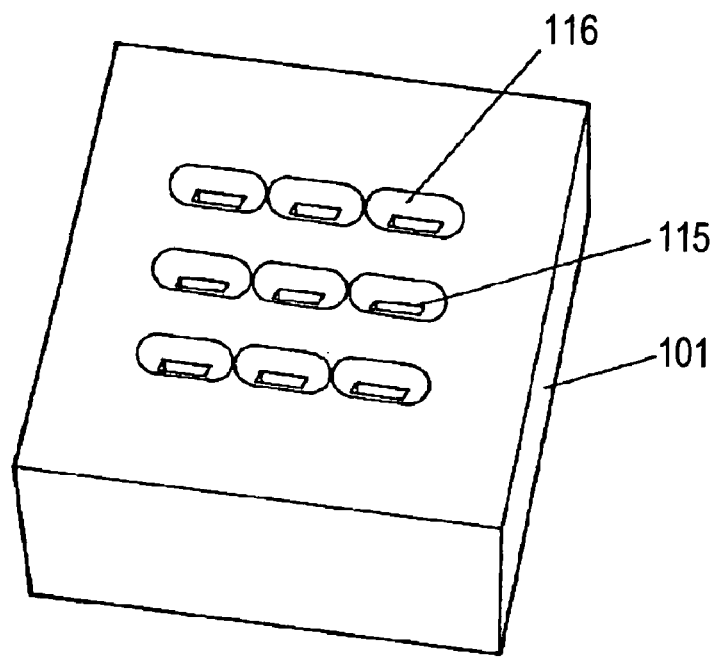
FIG. 41 is a perspective view of a further extracellular potential measuring device according to Embodiment 2.
Figure 42:
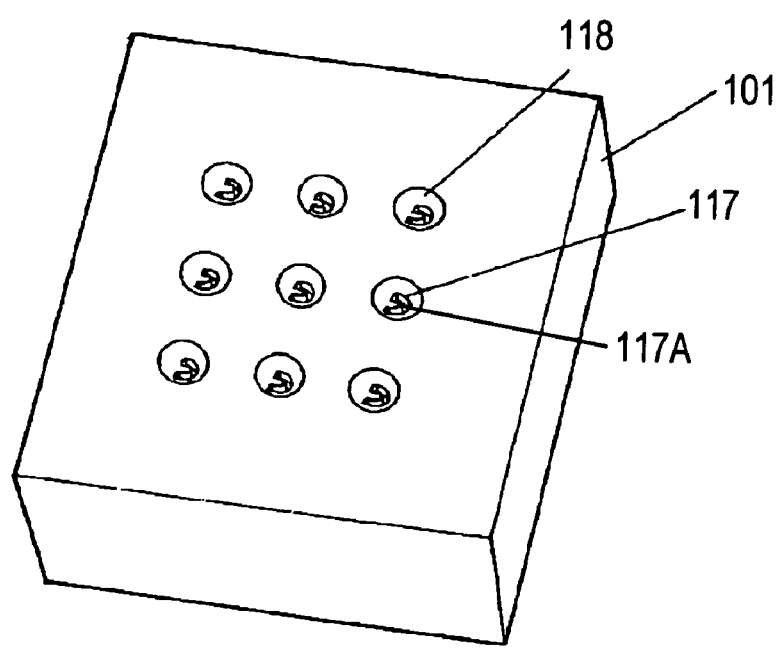
FIG. 42 is a perspective view of the extracellular potential measuring device shown in FIG. 41.

The cross section of through-holes 104 and 109a, 109b according to Embodiment 2 is circular or oval, but may be rectangular or U-shaped. FIGS. 41 and 42 are perspective views of extracellular potential measuring devices having through-holes 115 and 117 having rectangular and U-shaped cross sections, respectively. When through-hole 115 has a rectangular cross section, as shown in FIG. 41, pocket 116 is approximately semi-cylindrical with a round end and a round end. When through-hole 117 has a U-shaped cross section, as shown in FIG. 42, pocket 118 is substantially semispherical.

Pocket 116 having substantially semi-cylindrical shape is suitable to cell 108 having a long and narrow shape (e.g. a ganglion cell extracted from *Lymnaea stagnalis*).

A combination of pocket 118 having the semi-spherical shape and through-hole 117 having the U-shaped cross section is effective for a cell tending to deform while passing through, e.g. through-hole 104. More specifically, through-hole 17 having the U-shaped cross section reduces the minimum width of opening 117A while not reducing the volume of culture solution 107 to be filled into through-hole 117 so much. This can prevent cell 108 from falling into through-hole 117 and being damaged.

Sizes of pockets 103, 116 and 118 and Sizes of through-holes 104, 115 and 117 are determined in accordance with size, shape and properties of cell 108. Pockets 103, 116 and 118 having diameters ranging from 10 to 100 μm and through-holes 104, 115, and 117 having diameters ranging 1 to 10 μm allows activity of a cell having a diameter ranging substantially from 5 to 100 μm to be detected.

A method for manufacturing the extracellular potential measuring device according to Embodiment 2 will be described. FIGS. 29 to 34 are cross sectional views of extracellular potential measuring device 151 according to Embodiment 2 shown in FIG. 26 for illustrating the method for manufacturing device 151.

Figure 29:
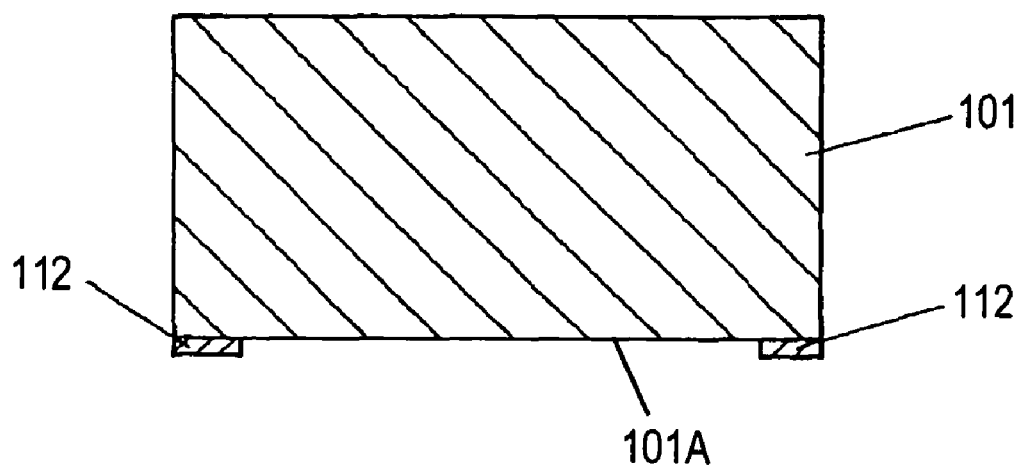
FIG. 29 is a cross sectional view of the extracellular potential measuring device for illustrating a method for manufacturing the device according to Embodiment 2.
Figure 30:
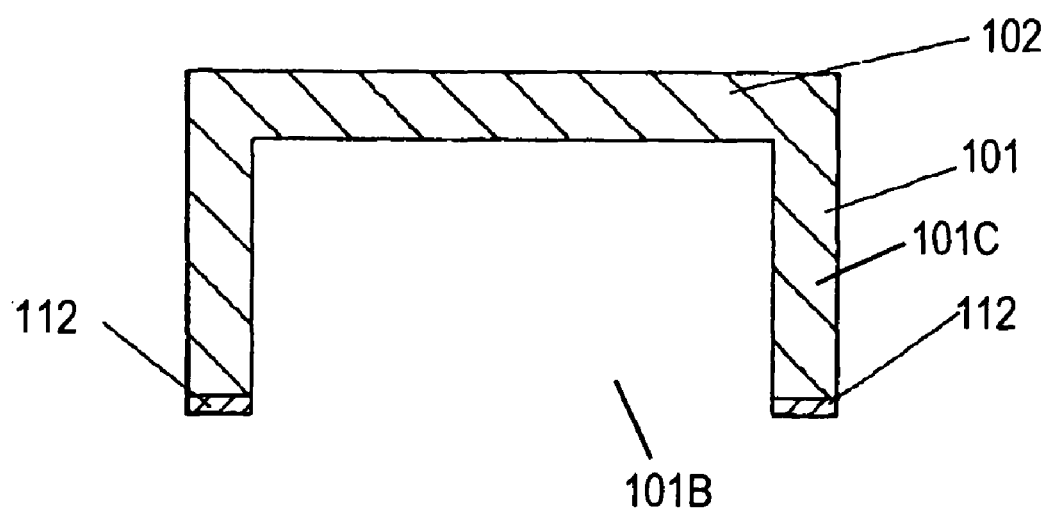
FIG. 30 is a cross sectional view of the extracellular potential measuring device for illustrating a method for manufacturing the device according to Embodiment 2.

Resist mask 112 is formed on surface 101A of substrate 101 made of silicon, as shown in FIG. 29, and then, substrate 101 is etched by a predetermined depth from surface 101A so as to form recess 101B, so that plate portion 102 supported by ridge 101C is formed at the upper part of substrate 101, as shown in FIG. 30. Resist mask 112 is then removed.

Figure 31:
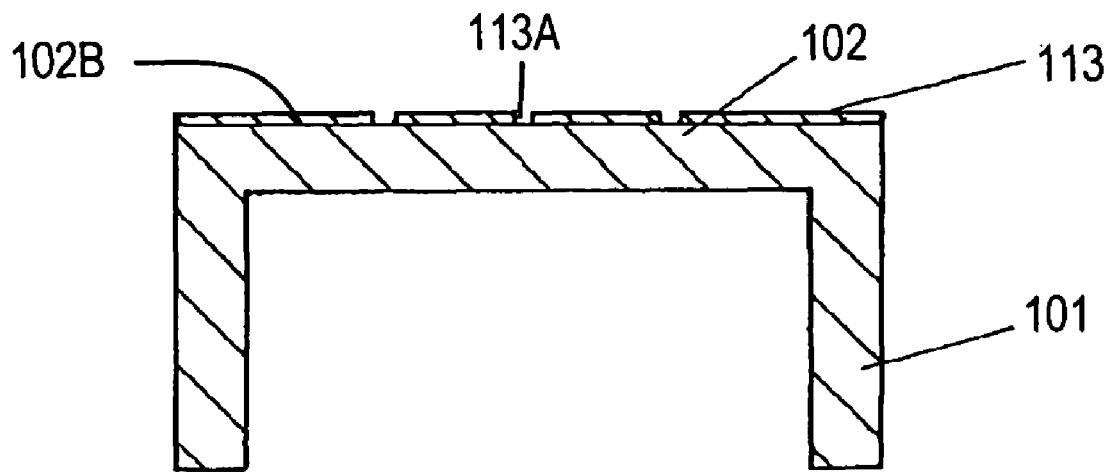
FIG. 31 is a cross sectional view of the extracellular potential measuring device for illustrating a method for manufacturing the device according to Embodiment 2.

Next, as shown in FIG. 31, resist mask 113 is formed on upper surface 102B of plate portion 102. Resist mask 113 has an etching hole 113A having a cross section substantially identical to a cross section of a predetermined shape of through-holes 104.

Figure 32:
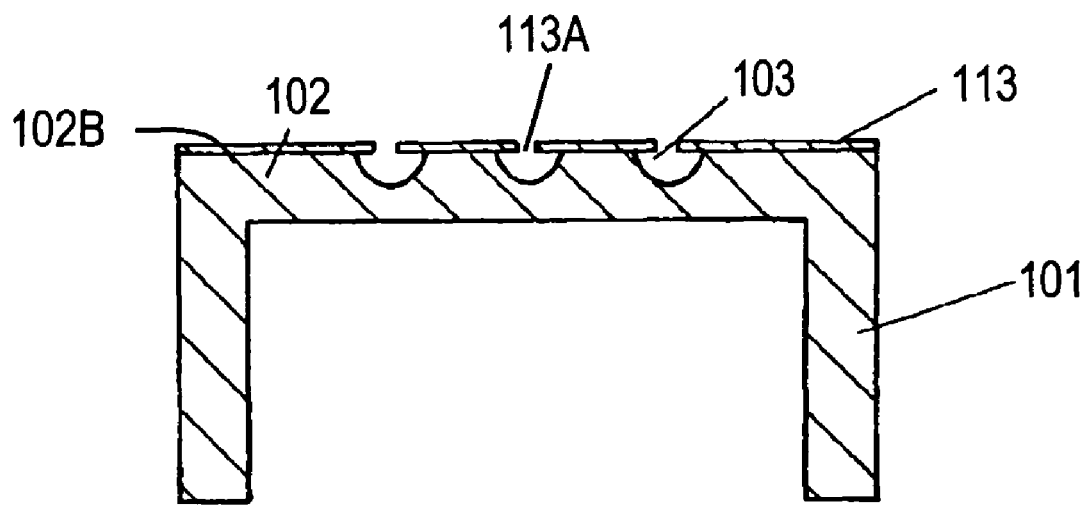
FIG. 32 is a cross sectional view of the extracellular potential measuring device for illustrating a method for manufacturing the device according to Embodiment 2.

Then, as shown in FIG. 32, plate portion 102 is dry-etched through etching holes 113A only with the gas for accelerating the etching.

For substrate 101 made of silicon, the gas for accelerating the etching may employ $SF_6$, $CF_4$, and $XeF_2$. These gases accelerate the etching not only in a direction orthogonal to resist mask 113, but also in a direction parallel to mask 113. Consequently, as shown in FIG. 32, substrate 101 is etched to have openings 113A having semispherical shapes having centers at the openings, thereby forming pockets 103.

Figure 33A:
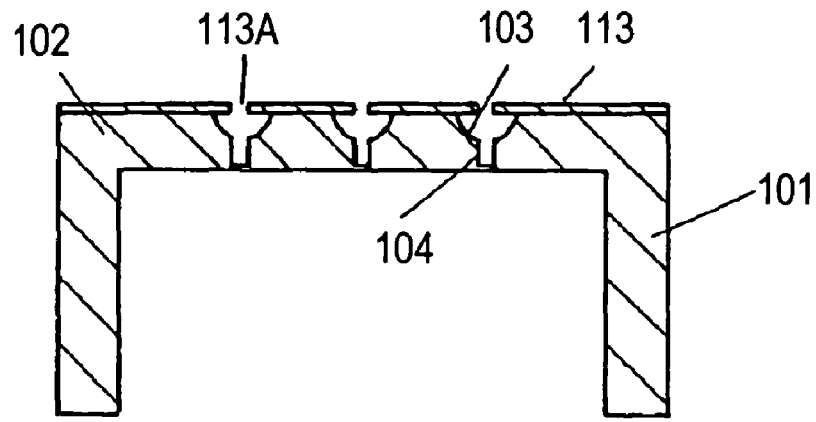
FIG. 33A is a cross sectional view of the extracellular potential measuring device for illustrating a method for manufacturing the device according to Embodiment 2.
Figure 33B:
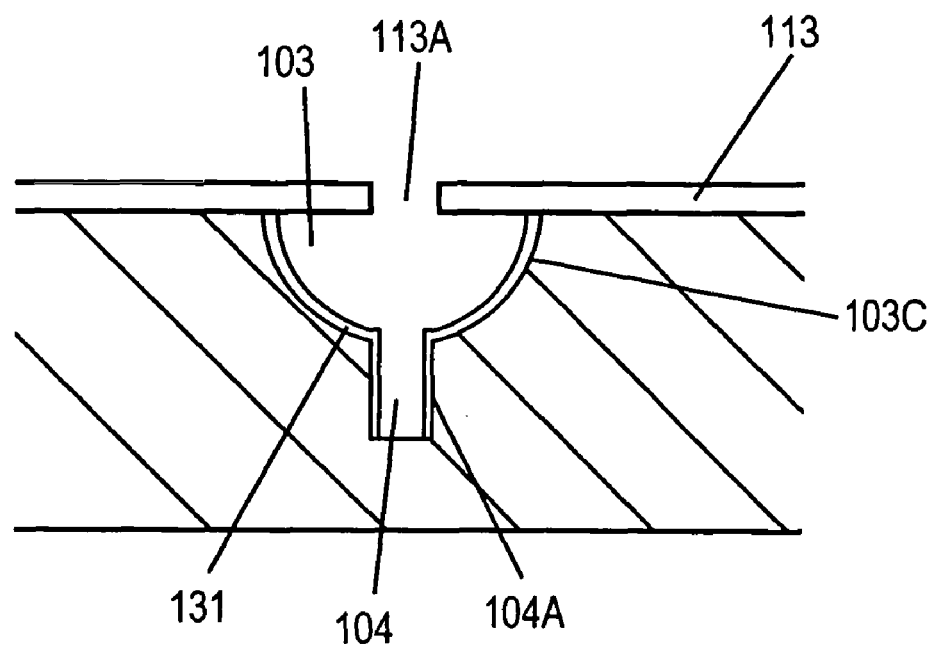
FIG. 33B is a cross sectional view of the extracellular potential measuring device for illustrating a method for manufacturing the device according to Embodiment 2.

Then, as shown in FIG. 33A, through-hole 104 extending from pocket 103 on substrate 101 is formed. Through-hole 104 is formed by dry-etching while the gas for accelerating the etching and gas for suppressing the etching are used alternately, and the dry-etching terminates before reaching plate portion 102. The gas for suppressing the etching may be $CHF_3$, $C_4F_8$, etc. A ratio between a time for using the gas for accelerating the etching and a time for using the gas for suppressing the etching is controlled, and the dry-etching of substrate 101 proceeds only perpendicularly beneath resist holes 113A similarly to Embodiment 1. In this process, as shown in FIG. 33B, the gas for suppressing the etching forms protective film 131 on inner surface 103C of pocket 103 and wall surface 104A of hole 104.

The cross section of hole 104 may has a shape of rectangular, U-shaped or a combination of these.

Figure 34:
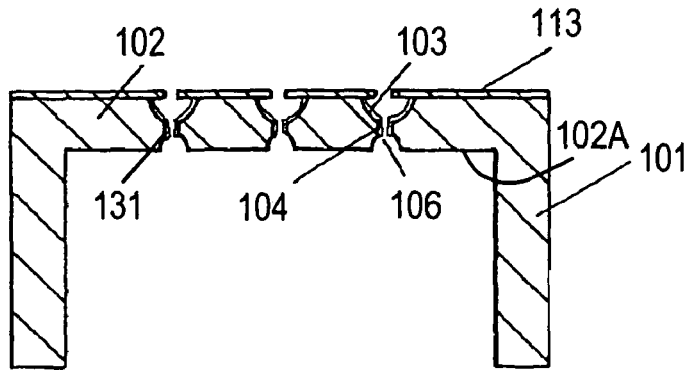
FIG. 34 is a cross sectional view of the extracellular potential measuring device for illustrating a method for manufacturing the device according to Embodiment 2.

Next, as shown in FIG. 34, substrate 101 is etched only with the gas for accelerating the etching. Since the wall surfaces of pocket 103 and hole 104 are coated with protective film 131, the gas for accelerating the etching allows hole 104 to be etched only towards lower surface 102A of plate portion 102, thereby providing pocket 106.

Protective film 131, upon an insufficient thickness may cause the wall surfaces of pockets 103 and holes 104 to be etched. To avoid this, after the formation of holes 104, protective film 131 may be thickened by applying the gas for suppressing the etching onto the wall surfaces. The thickness of protective films 131 can be controlled by changing the ratio between the time for using the gas for accelerating the etching and the time for using the gas for suppressing the etching. This operation provides pockets 103 and 106 having curved surfaces and through-holes 104 communicating with the pockets.

Then, as shown in FIG. 26, detector electrodes 105a and 105b are formed near pockets 106 by an ordinary method for forming a thin film. Since pocket 106 has a diameter larger than that of through-holes 104, detector electrodes 105a and 105b may not necessarily be made precisely, thus being formed easily.

A method for manufacturing an extracellular potential measuring device shown in FIG. 35 will be described. FIGS. 37A to 40 are cross sectional views of the device shown in FIG. 35 for illustrating the method for manufacturing the device.

First, pocket 103 is formed in the same manner as pocket 103 of device 151 shown in FIGS. 29 to 32.

Figure 37A:
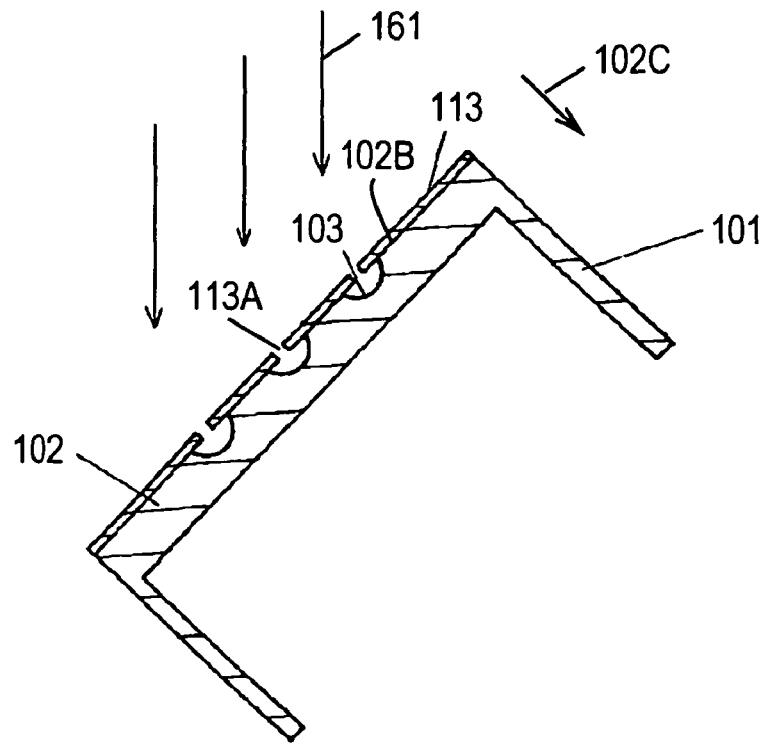
FIG. 37A is a cross sectional view of the extracellular potential measuring device shown in FIG. 35 for illustrating a method for manufacturing the device.
Figure 37B:
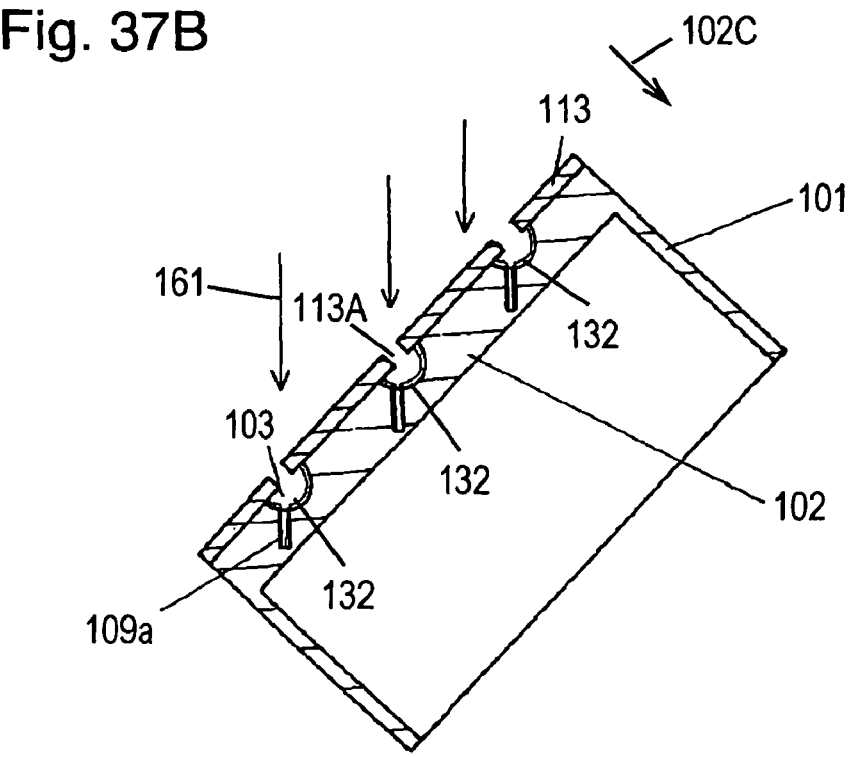
FIG. 37B is a cross sectional view of the extracellular potential measuring device shown in FIG. 35 for illustrating a method for manufacturing the device.

Then, as shown in FIG. 37A, substrate 101 is dry etched alternately with gas for accelerating the etching and gas for suppressing the etching, while upper surface 102B of substrate 101 inclines by 45° with respect to direction 61 in which ions of the etching gas flow. The gas for accelerating the etching may be $XeF_2$, $CF_4$ and, $SF_6$. The gas for suppressing the etching may be $CHF_3$ and $C_4F_8$. Substrate 101 is etched alternately with these gases, hence providing protective film 132 made of $CF_2$ polymer on an etched wall, as shown in FIG. 37B. Protective film 132 allows the etching to proceed only downward from etching hole 113A, thereby forming through-hole 109a.

Substrate 101 can be etched only downward from etching hole 113A similarly to Embodiment 1, so that the detailed description is not repeated here.

During the formation of through-holes 109a by the etching, the inclining angle of substrate 101 is limited by the shape of etching hole 113A and the thickness of resist mask 113. For example, when etching hole 113A has a diameter of 1 μm and resist mask 113 has a thickness of 1 μm, direction 161 necessarily incline by an angle smaller than 45° with respect to thickness direction 102C of substrate 101 due to geometrical limitations. Otherwise, substrate 101 cannot be etched.

Figure 39:
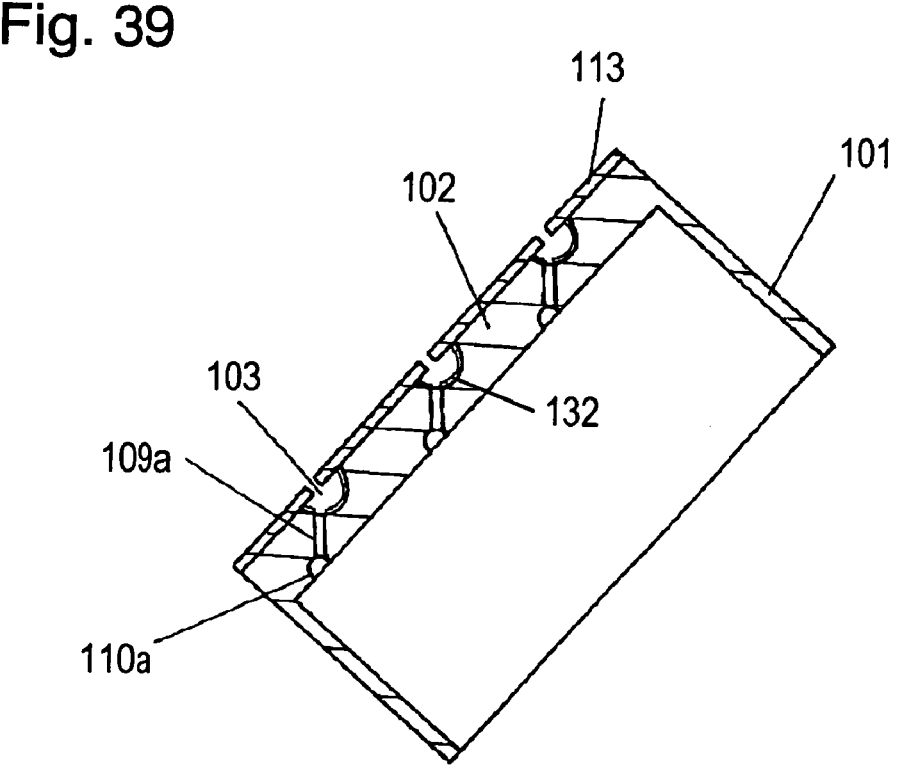
FIG. 39 is a cross sectional view of the extracellular potential measuring device shown in FIG. 35 for illustrating a method for manufacturing the device.

Next, substrate 101 is etched only with the gas for accelerating the etching, and hole 109a are etched only at a side towards lower surface 102A of plate portion 102 since protective film 132 is formed on the wall surfaces of pockets 103 and holes 109a by the etching with the gas for suppressing the etching. Thus, pockets 110a are provided, as shown in FIG. 39.

Figure 38:
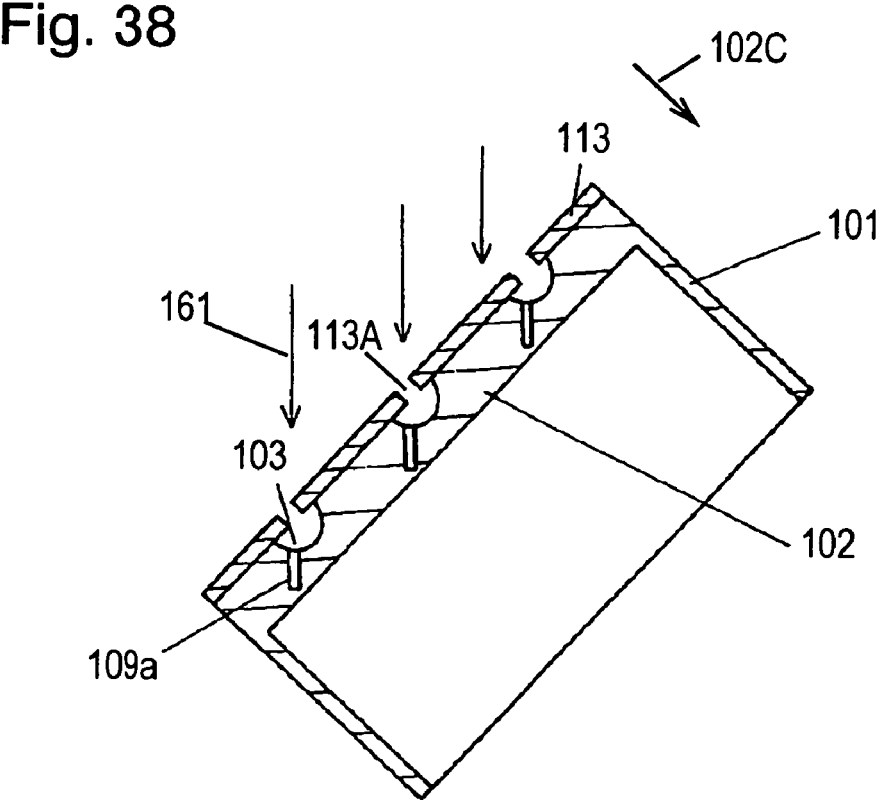
FIG. 38 is a cross sectional view of the extracellular potential measuring device shown in FIG. 35 for illustrating a method for manufacturing the device.
Figure 40:
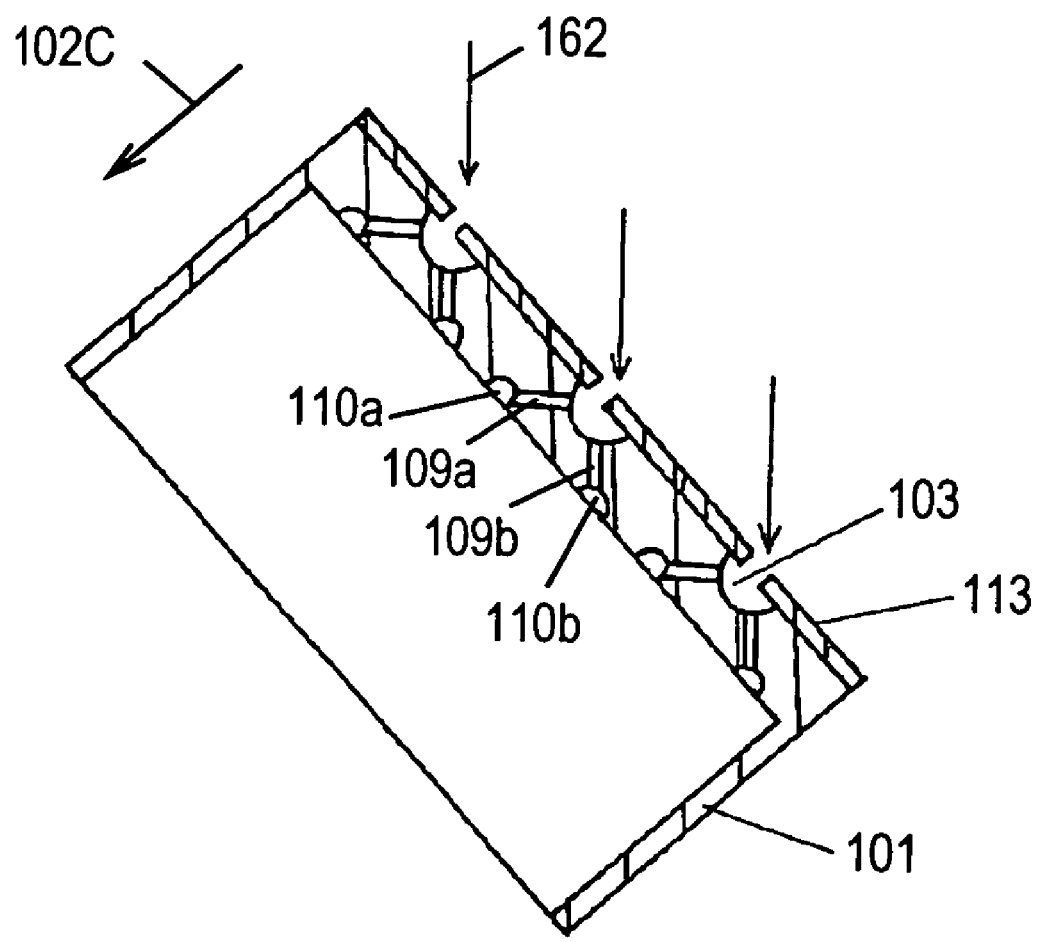
FIG. 40 is a cross sectional view of the extracellular potential measuring device shown in FIG. 35 for illustrating a method for manufacturing the device.

Then, as shown in FIG. 40, hole 109b is formed by having substrate 101 incline with respect to direction 162, and by alternately using ions of the gas for accelerating the etching and ions of gas for suppressing the etching both flowing in direction 162 symmetrical to direction 161 about thickness direction 102C shown in FIG. 38. Then, pockets 110b are formed only with the gas for accelerating the etching. Direction 162 can be asymmetrical with direction 161 about direction 102C to obtain the same effects. Resist mask 113 is removed after the etching.

Then, as shown in FIG. 35, in an ordinary method of forming a thin film on the lower surface of substrate 101, detector electrodes 111a and 111b mainly made of gold are formed near pockets 110a and 110b. Through-holes 109a and 109b communicating with pockets 103 can be made less precisely than electrodes 105a and 105b shown in FIG. 27, so that detector electrodes 111a and 111b can be formed easily.

Thus, through-holes 109a, 109b and pockets 110a, 110b extending from pockets 103 are formed, as shown in FIG. 35. In this etching process, the angle between direction 161 in which ions of plasma of the etching gas flow and thickness direction 102C of substrate 101 is 45°. This inclining angle is preferably not more than 89° under consideration of productivity, and more preferably, ranges from 20 to 70°.

Thus, through-holes 109a and 109b are covered by cell 108 more likely than any of through-holes 109a and 109b when the cell is held in pocket 103. This increases the chance of detecting extracellular potential with detector electrodes 111a and 111b provided inside pockets 110a and 11b.

Sizes of pockets 103 and through-holes 109a and 109b are determined according to a size, shape and properties of examined cell 8. Pocket 103 having a diameter ranging from 10 to 100 μm and through-holes 109a and 109b having diameters ranging from 1 to 10 μm allows an extracellular potential of a cell having a diameter ranging from 5 to 100 μm to be measured.

The diameters of pockets 110a and 111b is determined according to the diameters of through-holes 109a and 109b and fluid properties of culture solution 107. According to fluid analysis by a finite element method, it was confirmed that culture solution 107 having the same fluid properties as water stably forms a meniscus when through-holes 109a and 109b have diameters of 5 μm and pockets 110a and 110b have diameters of 10 μm.

Figure 44:
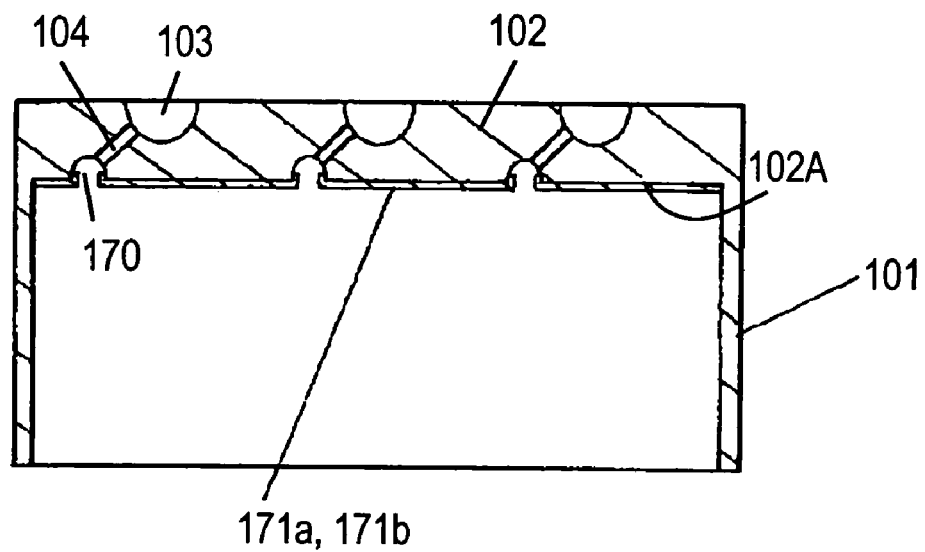
FIG. 44 is a cross sectional view of a still further extracellular potential measuring device according to Embodiment 2.
Figure 45:
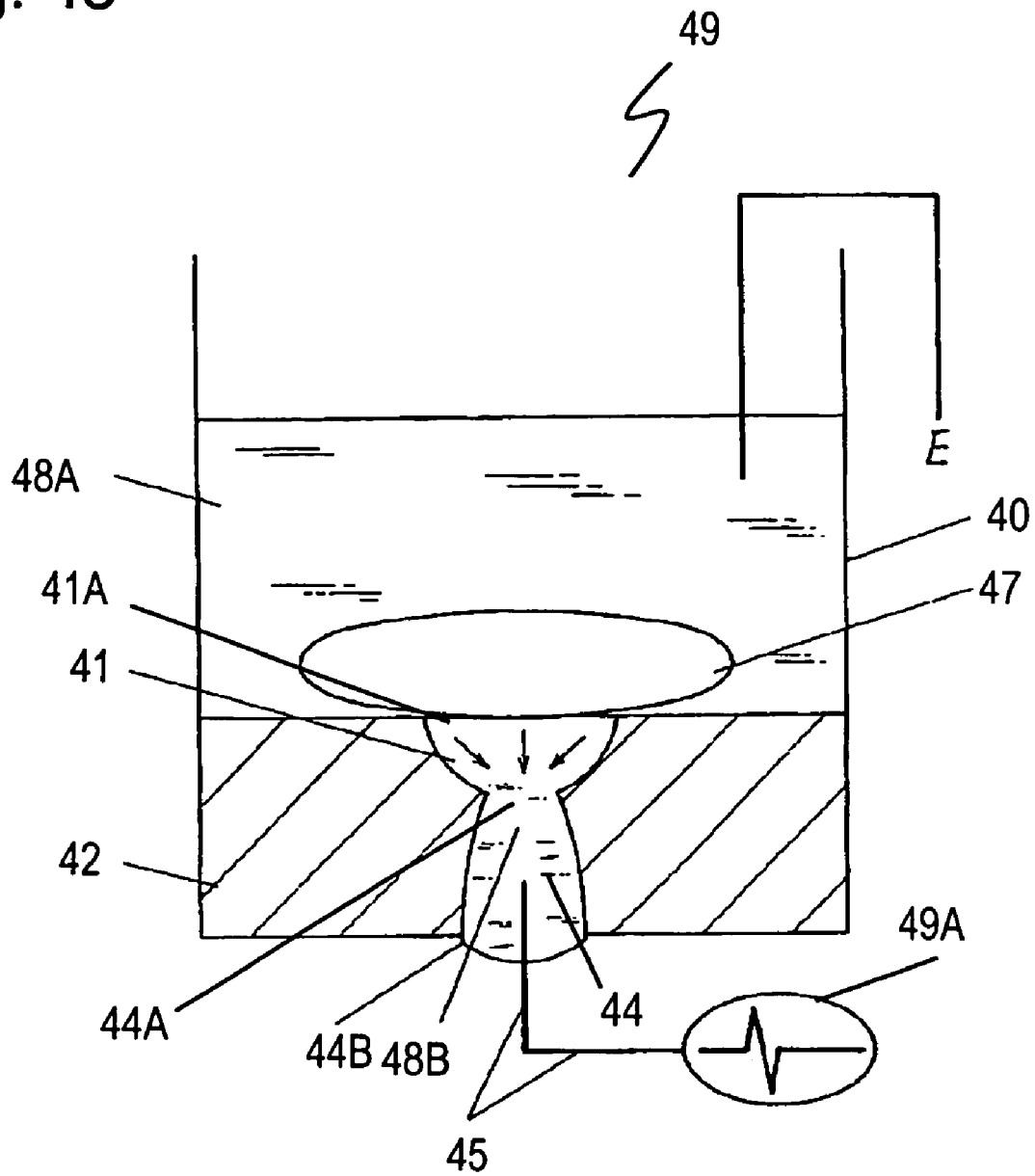
FIG. 45 is a cross sectional view of a conventional extracellular potential measuring device.

FIG. 44 shows a further extracellular potential measuring device according to Embodiment 2. In this device, pocket 170 equivalent to pocket 106 shown in FIG. 26 is formed in the opening of through-hole 4 in surface 2B formed in extracellular potential measuring device 51 shown in FIG. 3 according to Embodiment 1. In addition, electrodes 171a and 171b equivalent to electrodes 105a and 105b shown in FIG. 3, respectively, are formed near pocket 170.

Figure 43:
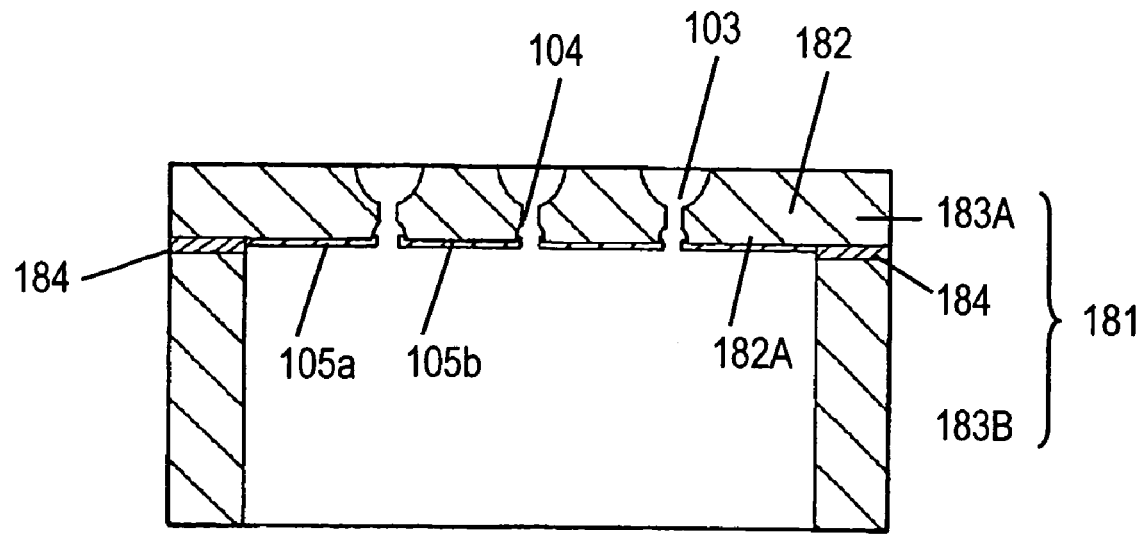
FIG. 43 is a cross sectional view of a still further extracellular potential measuring device according to Embodiment 2.

FIG. 43 is a cross sectional view of a still further extracellular potential measuring device according to Embodiment 2. In the extracellular potential measuring devices shown in FIGS. 25 to 42, substrate 101 is made of silicon substrate 1. In the device shown in FIG. 43, in stead of substrate 101 made of silicon, SOI substrate 181 formed of silicon layers 183A and 183B, and silicon oxide layer 184 may be employed. Silicon oxide layer 183A is provided on an outer rim of lower surface 182B of silicon layer 183A corresponding to plate portion 182, and silicon layer 182B is provided on silicon oxide layer 183A. Dry-etching terminates at silicon oxide layer 184, thereby allowing plate portion 182 to have a precise thickness, and facilitating the formation of through-holes 104 by the etching.

Electrodes 105a, 105b, 111a, 111b, 171a and 171b extend to the inner walls of pockets 106, 170, 110a and 110b according to Embodiment 2. However, similarly to electrodes 5a and 5b of Embodiment 1 shown in FIG. 3, these detector electrodes can be formed only on lower surfaces 102A and 2A of plate portions 102 and 2, without extending up to the inner walls of the pockets.

According to Embodiment 2, pockets 103 and through-holes 104 are formed after substrate 101 is structured to have recess 101A in which lower surface 102A of plate portion 102 is formed, and to have ridge 101C supporting plate portion 102. However, an extracellular potential measuring device with the same structure can be obtained by forming pockets 103 and through-holes 104 before substrate 101 is structured to have recess 101A in which lower surface 102A of plate portion 102 is formed, and to have ridge 101C supporting plate portion 102.

According to Embodiments 1 and 2, as long as plate portions 2 and 102 have the same shapes as those of Embodiments 1 and 2; the same effects can be obtained regardless of shapes of portions of substrates 1 and 101 other than plate portions 2 and 102.

INDUSTRIAL APPLICABILITY

An extracellular potential measuring devices according to the present invention can provide efficient and stable measurement of physicochemical changes in activities of call with a detector electrode.

REFERENCE NUMERALS

1 Substrate
2 Plate Portion
3 Pocket
4 Through-Hole
5 Detector Electrode
5a, 5b Detector Electrode
6 Culture Solution
8 Examined Cell
10a, 10b Through-Hole
11a, 11b Detector Electrode 12 Resist Mask
13 Resist Mask
14 Through-Hole
15 Through-Hole
16 Pocket
17 Through-Hole
18 Pocket
101 Substrate
102 Plate Portion
103 Pocket
104 Through-Hole
105a, 105b Detector Electrode
106 Pocket
107 Culture Solution
108 Cell to Be Examined
109a, 109b Through-Hole
110a, 110b Second Pocket
111a, 111b Detector Electrode
112 Resist Mask
113 Resist Mask

The invention claimed is:

1. An extracellular potential measuring device for measuring an extracellular potential of a cell, comprising:
a plate portion having a first surface and a second surface opposite to the first surface, the plate portion having a first pocket formed therein and a first through-hole formed therein, the first pocket having an opening which opens to the first surface, the first through-hole having a first opening and a second opening, and communicating to the second surface from a first position on an inner wall of the first pocket, the first position on the inner wall of the first pocket being closer to the opening of the first pocket than a deepest point of the first pocket,
wherein the first opening of the first through-hole opens to the second surface of the plate portion, and the second opening of the first through-hole opens to the first pocket and is arranged to be closed by the cell.

2. The extracellular potential measuring device according to claim 1, further comprising a first electrode provided on the second surface of the plate portion and around the first opening of the first through-hole which opens to the second surface of the plate portion.

3. The extracellular potential measuring device according to claim 2, wherein the plate portion has a second pocket formed therein at a portion of the first through-hole which opens to the second surface, the second pocket flaring towards the second surface of the plate portion.

4. The extracellular potential measuring device according to claim 3, wherein the first electrode extends to at least a portion of a surface of the second pocket.

5. The extracellular potential measuring device according to claim 3, further comprising a second electrode provided over the second surface of the plate portion and around the first opening of the first through-hole.

6. The extracellular potential measuring device according to claim 5, wherein the second electrode extends to at least a portion of a surface of the second pocket.

7. The extracellular potential measuring device according to claim 2, wherein the plate portion has a second through-hole formed therein, the second through-hole communicating with the second surface from a second position closer to the opening of the first pocket than the deepest point of the first pocket.

8. The extracellular potential measuring device according to claim 7, further comprising a second electrode provided over the second surface of the plate portion and around an opening of the second through-hole.

9. The extracellular potential measuring device according to claim 2, wherein the plate portion has a second pocket formed therein at the first opening of the first through-hole which opens to the second surface, the second pocket flaring towards the second surface of the plate portion.

10. The extracellular potential measuring device according to claim 2, further comprising a second electrode provided over the second surface of the plate portion and around the first opening of the first through-hole.

11. The extracellular potential measuring device according to claim 1, wherein the plate portion has a second pocket formed therein at a portion of the first through-hole which opens to the second surface, the second pocket flaring towards the second surface of the plate portion.

12. The extracellular potential measuring device according to claim 1, wherein the first through-hole includes a portion having a uniform cross section.

13. The extracellular potential measuring device according to claim 1, wherein the first through-hole has one of a rectangular cross section and a U-shaped cross section.

14. The extracellular potential measuring device according to claim 1, wherein the plate portion contains silicon.

15. The extracellular potential measuring device according to claim 14, further comprising:
a silicon oxide layer provided on the second surface of the plate portion; and
a silicon layer provided on the silicon oxide layer, such that the silicon oxide layer is disposed between the plate portion and the silicon layer.

16. The extracellular potential measuring device according to claim 15, wherein the silicon oxide layer is provided on an outer rim of the second surface of the plate portion.

17. The extracellular potential measuring device according to claim 1,
wherein the opening of the first pocket has a diameter ranging from 10 to 100 μm, and
wherein the second opening of the first through-hole which opens to the first pocket has a width ranging from 1 to 10 μm.

18. The extracellular potential measuring device according to claim 1, wherein the plate portion has a second through-hole formed therein, and the second through-hole communicating with the second surface from a second position which is closer to the opening of the first pocket than the deepest point of the first pocket.

19. The extracellular potential measuring device according to claim 18, wherein the plate portion has a second pocket formed therein at the first opening of the first through-hole which opens to the second surface, the second pocket flaring towards the second surface of the plate portion.

20. The extracellular potential measuring device according to claim 9, further comprising a second electrode provided over the second surface of the plate portion and around the first opening of the first through-hole.

21. The extracellular potential measuring device according to claim 20, wherein the second electrode extends to at least a portion of a surface of the second pocket.

22. The extracellular potential measuring device according to claim 18, wherein the second through-hole includes a portion having a uniform cross section.

23. The extracellular potential measuring device according to claim 18, wherein the second through-hole has one of a rectangular cross section and a U-shaped cross section.

24. The extracellular potential measuring device according to claim 18,
wherein the first opening of the first pocket has a diameter ranging from 10 to 100 μm, and wherein an opening of the second through-hole which opens to the first pocket has a width ranging from 1 to 10 µm.

25. A method for manufacturing an extracellular potential measuring device, said method comprising:
providing a plate portion having a first surface and a second surface opposite to the first surface;
providing a resist mask having an etching hole therein on the first surface of the plate portion;
forming a first pocket in the plate portion around the etching hole by etching, the first pocket having an opening which opens to the first surface of the plate portion;
forming a first through-hole communicating to the second surface of the plate portion from a first position closer to the opening of the first pocket than a deepest point of the first pocket; and
forming a first electrode on the second surface of the plate portion and around the opening of the first through-hole which opens to the second surface of the plate portion.

26. The method according to claim 25, wherein said forming the first pocket comprises forming the first pocket in the plate portion by dry-etching only with first gas for accelerating etching.

27. The method according to claim 25, wherein the first through-hole has a portion having a uniform cross section.

28. The method according to claim 25, wherein said forming the first through-hole comprises:
forming a hole from the first position of the first pocket towards the second surface of the plate portion; and
forming a second pocket extending from the hole and flaring towards the second surface of the plate portion so as to allow the hole communicates to the second surface of the plate portion.

29. The method according to claim 28, wherein the first electrode extends to at least a portion of a surface of the second pocket.

30. The method according to claim 25, wherein said forming the first through-hole comprises forming the first through-hole in the plate portion by dry etching with first gas for accelerating etching and second gas for suppressing etching.

31. The method according to claim 30, wherein said forming the first through-hole comprises forming the first through-hole in the plate portion by alternately using the first gas and the second gas.

32. The method according to claim 30, wherein said forming the first through-hole comprises forming the first through-hole in the plate portion by having the first gas and the second gas flow in a first direction through the etching hole.

33. The method according to claim 32, wherein an angle between the first direction and a thickness direction of the plate portion from the first surface to the second surface is not more than 89°.

34. The method according to claim 33, wherein the angle between the first direction and the thickness direction of the plate portion ranges from 20° to 70°.

35. The method according to claim 34, wherein the angle between the first direction and the thickness direction of the plate portion is 45°.

36. The method according to claim 25 further comprising:
forming a second through-hole communicating to the second surface of the plate portion from a second position is closer to the opening of the first pocket than the deepest point of the first pocket; and
forming a second electrode on the second surface of the plate portion and around an opening of the second through-hole which opens to the second surface of the plate portion.

37. The method according to claim 36, wherein the second through-hole has a portion having a uniform cross section.

38. The method according to claim 36, wherein said forming the second through-hole comprises forming the second through-hole in the plate portion by dry-etching with first gas for accelerating etching and second gas for suppressing etching.

39. The method according to claim 38, wherein said forming the second through-hole comprises forming the second through-hole in the plate portion by dry-etching by alternately using the first gas and the second gas.

40. The method according to claim 36, wherein said forming the second through-hole comprises:
forming a hole from the second position of the first pocket towards the second surface of the plate portion; and
forming a second pocket extending from the hole and flaring towards the second surface of the plate portion so as to allow the hole communicate to the second surface of the plate portion.

41. The method according to claim 40, wherein the first electrode extends to at least a portion of a surface of the second pocket.

42. The method according to claim 40,
wherein said forming the first through-hole comprises forming the first through-hole in the plate portion by having the first gas and the second gas flow in a first direction through the etching hole; and
wherein said forming the second through-hole comprises forming the second through-hole in the plate portion by having the first gas and the second gas flow in a second direction through the etching hole.

43. The method according to claim 42,
wherein an angle between the first direction and a thickness direction of the plate portion from the first surface to the second surface is not more than 89°, and
wherein an angle between the second direction and the thickness direction of the plate portion is not more than 89°.

44. The method according to claim 43, wherein the first direction and the second direction are symmetrical to each other about the thickness direction of the plate portion.

45. The method according to claim 43, wherein the angle between the thickness direction of the plate portion and the first direction ranges from 20° to 70°.

46. The method according to claim 45, wherein the angle between the thickness direction of the plate portion and the first direction is 45°.

47. The method according to claim 43, wherein the angle between the thickness direction of the plate portion and the second direction ranges from 20° to 70°.

48. The method according to claim 47, wherein the angle between the thickness direction of the plate portion and the second direction is 45°.

49. The method according to claim 26, wherein the first gas contains one of $SF_6$, $CF_4$, and $XeF_2$.

50. The method according to claim 30, wherein the second gas contains at least one of $C_4F_8$ and $CHF_3$.

51. The method according to claim 38, wherein the first gas contains one of $SF_6$, $CF_4$, and $XeF_2$.

52. The method according to claim 38, wherein the second gas contains at least one of $C_4F_8$ and $CHF_3$.

53. A method for manufacturing an extracellular potential measuring device, said method comprising:
providing a plate portion having a first surface and a second surface opposite to the first surface;
providing a resist mask having an etching hole therein on the first surface of the plate portion;

forming a first pocket in the plate portion around the etching hole by etching, the first pocket having an opening which opens to the first surface of the plate portion;

forming a hole extending from the first pocket towards the second surface of the plate portion, the hole having a uniform cross section, and being positioned closer to the opening of the first pocket than the deepest point of the first pocket;

forming a second pocket extending from the hole towards the second surface of the plate portion, the second pocket having an opening which opens to the second surface as to allow the hole to communicate to the second surface, the second pocket flaring towards the second surface of the plate portion; and forming a first electrode on the second surface of the plate portion and around the opening of the second pocket.

54. The method according to claim 53, wherein said forming the first pocket comprises forming the first pocket in the plate portion by dry-etching only with first gas for accelerating etching.

55. The method according to claim 53, wherein said forming the hole comprises forming the hole by dry-etching with first gas for accelerating etching and second gas for suppressing etching.

56. The method according to claim 55, wherein the second gas contains at least one of $C4F_8$ and $CHF_3$.

57. The method according to claim 53, wherein said forming the second pocket comprises the second pocket by dry-etching only with first gas for accelerating etching.

58. The method according to claim 54, wherein the first gas contains one of $SF_6$, $CF_4$, and $XeF_2$.

59. The method according to claim 30, wherein the first gas contains one of $SF_6$, $CF_4$, and $XeF_2$.

60. The method according to claim 55, wherein the first gas contains one of $SF_6$, $CF_4$, and $XeF_2$.

61. The method according to claim 57, wherein the first gas contains one of $SF_6$, $CF_4$, and $XeF_2$.

* * * * *